United States Patent [19]
Aszodi et al.

[11] Patent Number: 5,710,147
[45] Date of Patent: Jan. 20, 1998

[54] 7-BENZYLOXYIMINO-CEPHALOSPORINS

[75] Inventors: Jozsef Aszodi, Pontault Combault; Patrick Fauveau, Livry Gargan, both of France

[73] Assignee: Roussel Uclaf, France

[21] Appl. No.: 499,168

[22] Filed: Jul. 7, 1995

[30] Foreign Application Priority Data

Jul. 19, 1994 [FR] France .................. 94 08912

[51] Int. Cl.$^6$ .................. A61K 31/545; C07D 501/24
[52] U.S. Cl. .................. 514/202; 540/222; 540/224
[58] Field of Search .................. 540/222, 224; 514/202

[56] References Cited

U.S. PATENT DOCUMENTS

| | | | |
|---|---|---|---|
| 3,887,549 | 6/1975 | Christensen | 260/243 C |
| 5,373,001 | 12/1994 | Aszodi et al. | 540/222 |
| 5,455,238 | 10/1995 | Aszodi et al. | 540/222 |

FOREIGN PATENT DOCUMENTS

| | | |
|---|---|---|
| 0038778 | 10/1981 | European Pat. Off. . |
| 0333154 | 9/1989 | European Pat. Off. . |
| 0551034 | 7/1993 | France . |

OTHER PUBLICATIONS

Article entitled: Formylation with formyl fluoride. vol. 82, Olah et al pp. 2380–2382 May 5, 1960.

*Primary Examiner*—Matthew V. Grumbling
*Assistant Examiner*—Pavanaram K. Sripada
*Attorney, Agent, or Firm*—Bierman, Muserlian & Lucas

[57] ABSTRACT

The syn isomer of (R) or (S) or (R,S) mixture, in the form of internal salts or salts with acids or bases of a compound of the formula

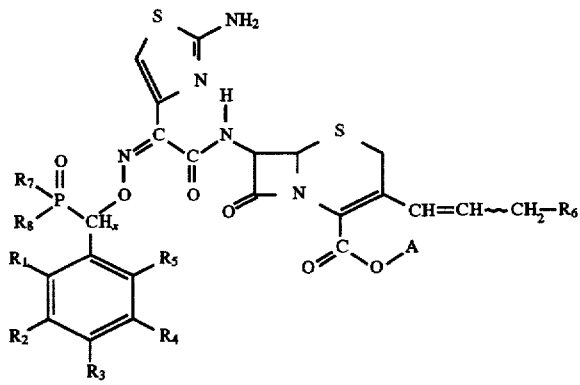

wherein the substituents are defined as in the specification having a very good antibiotic activity.

20 Claims, No Drawings

7-BENZYLOXYIMINO-CEPHALOSPORINS

OBJECTS OF THE INVENTION

It is an object of the invention to provide the novel compounds of formula I in their various forms to provide a novel process and intermediates for their preparation.

It is another object of the invention to provide novel antibiotic compositions and a method of treating bacterial infections in warm-blooded animals.

These and other objects and advantages of the invention will become obvious from the following detailed description.

THE INVENTION

The novel compounds of the invention are syn isomers of a compound of the formula

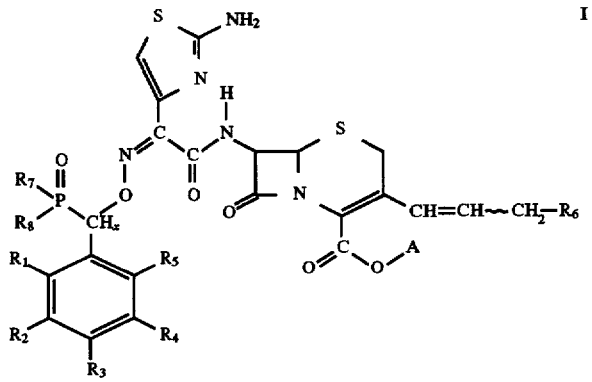

in (R) or (S) form or an (R,S) mixture or in the form of internal salts or salts with non-toxic, pharmaceutically acceptable acids or bases wherein $R_1$, $R_2$, $R_3$ and $R_5$ are individually selected from the group consisting of hydrogen, halogen, —OH, alkyl of 1 to 4 carbon atoms optionally substituted with at least one halogen, alkoxy of 1 to 4 carbon atoms, —SH, —NO$_2$, —CN, alkylthio of 1 to 4 carbon atoms, amino, alkylamino of 1 to 4 carbon atoms, dialkylamino of 2 to 8 carbon atoms, carbamoyl, alkylaminocarbonyl of 2 to 5 carbon atoms, dialkylaminocarbonyl of 3 to 9 carbon atoms, —COOH, alkoxycarbonyl of 2 to 5 carbon atoms, acyloxy of 1 to 8 carbon atoms, and

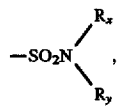

$R_x$ and $R_y$ are individually hydrogen or alkyl of 1 to 4 carbon atoms, $R_4$ is hydroxy or acyloxy of 1 to 8 carbon atoms, $R_7$ is selected from the group consisting of alkyl of 1 to 4 carbon atoms, —OH, alkoxy of 1 to 4 carbon atoms and phenyl, $R_8$ is —OH or alkoxy of 1 to 4 carbon atoms or $R_7$ and $R_8$ together are an alkylenedioxy of 2 to 8 carbon atoms, A is selected from the group consisting of hydrogen, an equivalent of an alkali metal, alkaline earth-metal, magnesium, ammonium and an amino organic base and the remainder of an easily cleavable ester or —COOA is —COO$^-$, the wavy line indicates —CH$_2$R$_6$ is in the E or Z position, $R_6$ in its quaternary ammonium form is selected from the group consisting of

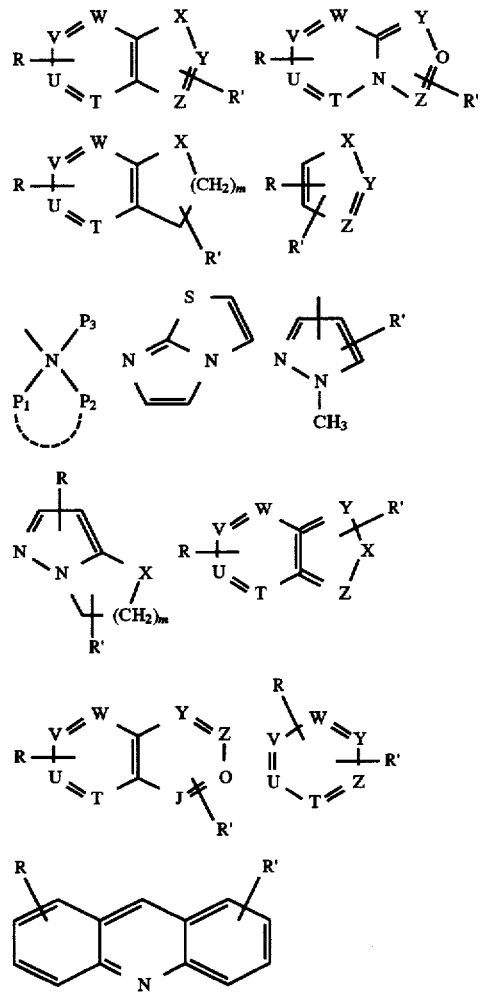

X is selected from the group consisting of —CH$_2$—, —NH—, —O— and —S—, Q, J, Y, T, U, V, W and Z are individually —CH— or —N— with each cyclic ring containing 1 to 5 heteroatoms with at least one being nitrogen and optionally substituted with at least one R or R', R and R' are individually selected from the group consisting of hydrogen, alkyl of 1 to 4 carbon atoms, alkoxy of 1 to 4 carbon atoms, halogen, —CN, —COOQ$_1$,

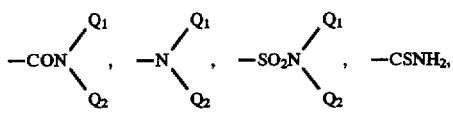

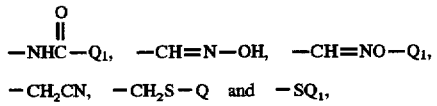

$Q_1$ and $Q_2$ are individually hydrogen or alkyl of 1 to 4 carbon atoms $P_1$, $P_2$ and $P_3$ are individually alkyl of 1 to 4 carbon atoms optionally substituted by R or R' and one may be —OH or $P_1$ and $P_2$ together with the nitrogen atom to which they are attached form a 5- or 6-member heterocyclic and m is 1, 2 or 3.

Examples of alkyl 1 to 4 carbon atoms are methyl, ethyl, propyl, isopropyl, butyl, isobutyl, sec-butyl or tert-butyl and examples of alkoxy of 1 to 4 carbon atoms are methoxy, ethoxy, propoxy, isopropoxy, butoxy, isobutoxy, sec-butoxy or tert-butoxy. Examples of alkylthio 1 to 4 carbon atoms are methylthio, ethylthio, propylthio, isopropylthio, butylthio, isobutylthio, sec-butylthio or tert-butylthio.

Examples of alkylamino of 1 to 4 carbon atoms are methylamino, ethylamino, propylamino, isopropyl-amino, butylamino, isobutylamino, sec-butylamino or tert-butylamino and examples of dialkylamino of 2 to 8 carbon atoms include dimethylamino, diethylamino, dipropylamino, diisopropylamino, dibutylamino, diisobutyl-amino, ethyl methylamino, propyl methylamino, butyl methylamino and propyl ethylamino.

Examples of (alkylamino) carbonyl of 2 to 5 carbon atoms are (methylamino) carbonyl, (ethylamino) carbonyl, (propylamino) carbonyl, (isopropylamino) carbonyl and (butylamino) carbonyl. Examples of alkoxycarbonyl of 2 to 5 carbon atoms include methoxycarbonyl and ethoxycarbonyl. Examples of (dialkylamino) carbonyl of 3 to 9 carbon atoms are (dimethylamino) carbonyl, (diethylamino) carbonyl and (dipropylamino) carbonyl.

Examples of acyloxy of an organic carboxylic acid of 1 to 8 carbon atoms are acetoxy, propionyloxy or benzoyloxy. Examples of alkylenedioxy of 2 to 8 carbon atoms are linear type or branched such as ethylenedioxy, trimethylenedioxy, 1,2-dimethylethylenedioxy and trimethylenedioxy substituted by one or two methyls, particularly twinned. Examples of halogen are fluorine, chlorine, bromine or iodine.

When $P_1$ and $P_2$ form a heterocycle with the nitrogen atom to which they are attached, examples are pyrrolidino, morpholino or piperidino. When $R_4$ is acyloxy, it is preferably acetoxy, propionyloxy or benzoyloxy.

Among the values of A are equivalents of sodium, potassium, lithium, calcium, magnesium or ammonium, an equivalent of an organic base such as methylamine, propylamine, trimethylamine, diethylamine, triethylamine, N,N-dimethylethanolamine, tris[(hydroxymethyl)amino] methane, ethanolamine, pyridine, picoline, dicyclohexylamine, morpholine, benzylamine, procaine, lysine, arginine, histidine, N-methylglucamine.

Examples of remainders of easily cleavable esters represented by A are methoxymethyl, ethoxymethyl, isopropyloxymethyl, α-methoxy ethyl, α-ethoxy ethyl, methylthiomethyl, ethylthiomethyl, isopropylthiomethyl, pivaloyloxymethyl, acetoxymethyl, propionyloxymethyl, butyryloxymethyl, isobutyryloxymethyl, valeryloxymethyl, isovaleryloxymethyl, tert-butylcarbonyloxymethyl, hexadecanoyloxymethyl, propionyloxyethyl, isovaleryloxyethyl, 1-acetyloxyethyl, 1-propionyloxyethyl, 1-butyryloxyethyl, 1-tert-butylcarbonyloxyethyl, 1-acetyloxypropyl, 1-hexa-decanoyloxyethyl, 1-propionyloxypropyl, 1-methoxycarbonyl-oxyethyl, methoxycarbonyloxymethyl, 1-acetyloxybutyl, 1-acetyloxyhexyl, 1-acetyloxyheptyl, phthalidyl, 5,6-dimethoxyphthalidyl, tert-butylcarbonylmethyl, allyl, 2-chloroallyl, methoxycarbonylmethyl, benzyl or tert-butyl.

Other remainders of ester groups which A can be are methoxyethoxymethyl, dimethylaminoethyl, cyanomethyl, tert-butoxycarbonylmethyl, 2,2-ethylenedioxyethyl, cyanoethyl, 2,2-dimethoxyethyl; 2-chloroethoxymethyl, 2-hydroxyethoxyethyl, 2,3-epoxypropyl, 3-dimethylamino, 2-hydroxypropyl, 2-hydroxyethyl, 2-methylaminoethoxymethyl, 2-aminoethoxymethyl, 3-methoxy 2,4-thiadiazol-5-yl, 2-tetrahydropyrannyl, 1-methoxy 1-methyl ethyl, 2-hydroxy 1-methyl ethyl, isopropyl; carbamoylmethyl, chloromethyl, 2-chloroethyl, acetylmethyl, 2-methylthioethyl or thiocyanatomethyl.

Other remainders of ester groups which A can be are 2-chloro 1-acetyloxyethyl, 2-bromo 1-acetyloxyethyl, 2-fluoro 1-acetyloxyethyl, 2-methoxy 1-acetyloxyethyl, 2-methyl 1-acetyloxypropyl, 1-methyl 1-acetyloxyethyl, 1-methoxyacetyloxyethyl, 1-acetylcarbonyloxyethyl, 1-hydroxyacetyloxyethyl, 1-formylcarbonyloxyethyl, 1-(2-thienyl)carbonyloxyethyl, 1-(2-furyl)carbonyloxyethyl, 1-(5-nitro 2-furyl)carbonyloxyethyl, 1-(2-pyrrolyl) carbonyloxyethyl, 1-(propionyloxycarbonyloxy)ethyl, 1-(propyloxycarbonyloxy)ethyl, 1-(isopropyloxycarbonyloxy)ethyl, 1-(methoxyethoxycarbonyloxy)ethyl, 1-(allyloxycarbonyloxy)ethyl, isopropyloxycarbonyl methyl, 1-[(2,3-epoxy propyl)oxycarbonyloxy]ethyl, 1-[(2-furyl) methyloxycarbonyloxy]ethyl, 1-(2-fluoro ethyl) oxycarbonyloxyethyl, 1-(methoxycarbonyloxy)propyl, 1-(methoxycarbonyloxy) 1-methyl ethyl, (methoxycarbonyloxy)chloromethyl, 1-(methoxycarbonyloxy) 2-chloroethyl, 1-(methoxycarbonyloxy) 2-methoxy ethyl, 1-(methoxycarbonyloxy)allyl, or

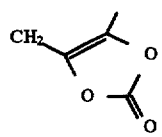

The products of formula I can also be in the form of a pure internal salt, in salified form or in a form combined with the acids of the solution, or also in the form of salts of bases at the level of the other carboxys or at the level of the hydroxy or groups carried by the phosphorus atom.

Among the acids with which the products of formula I can be salified are acetic acid, trifluoroacetic acid, maleic acid, tartaric acid, methanesulfonic acid, benzenesulfonic acid, p-toluenesulfonic acid, phosphoric acid, sulfuric acid, hydrochloric acid, hydrobromic acid, and hydroiodic acid.

Among the bases with which the products of formula I can be salified are bases corresponding to the salts mentioned above.

In a preferred method of the invention, $CO_2A$ is $CO_2^-$. The expression "in quaternary ammonium form" indicates that $R_6$ is linked by one or more of the nitrogen atoms which it contains.

$R_6$ is preferably selected from the group consisting of:

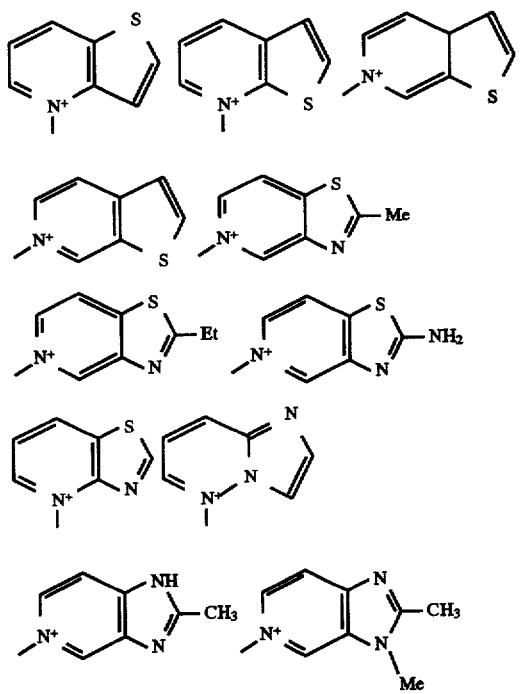

-continued

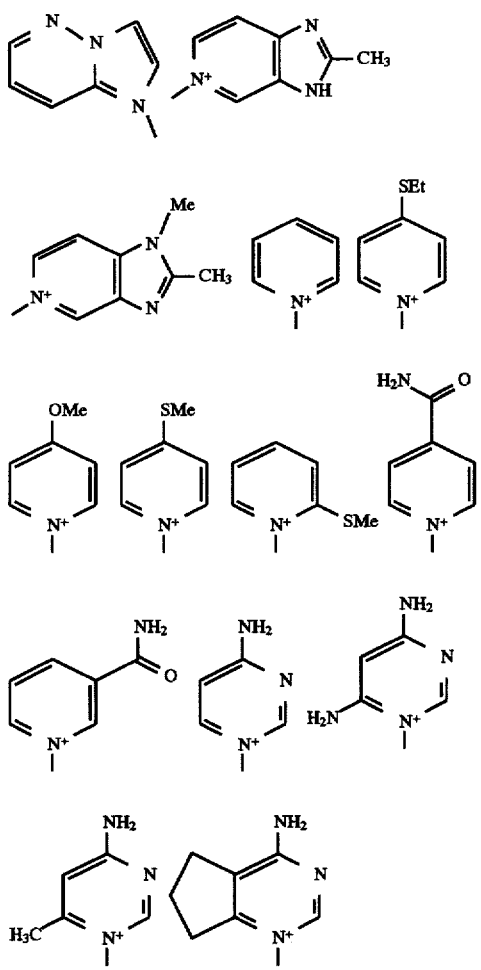

or also one of the following radicals:

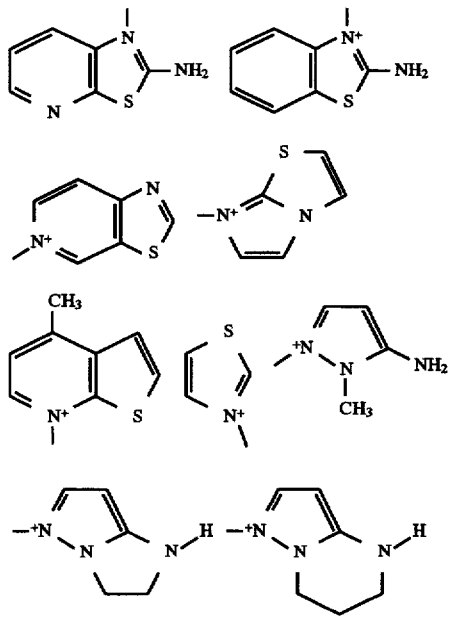

-continued

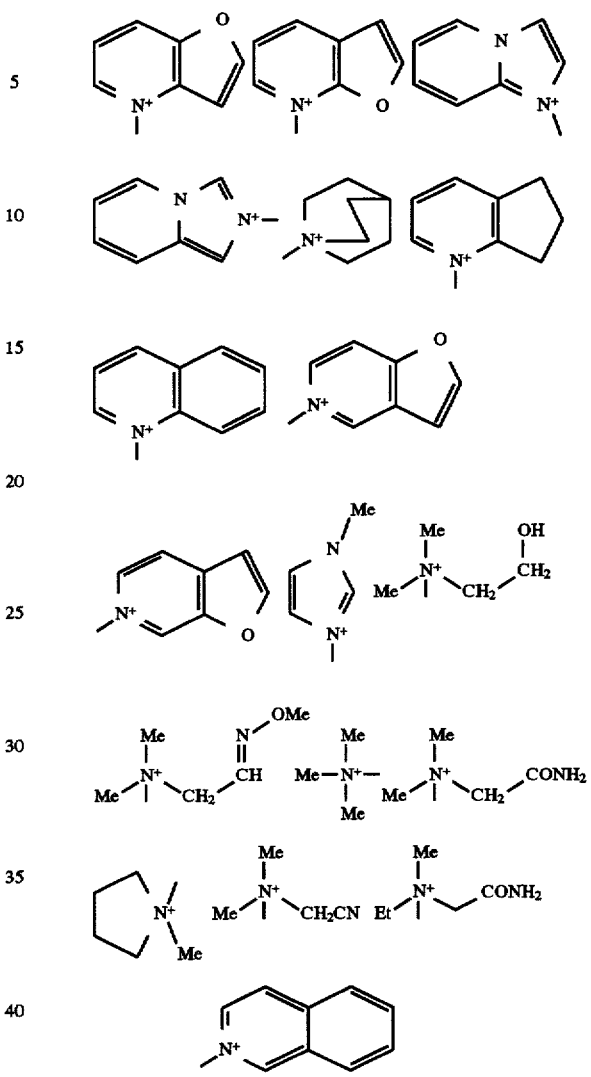

Among the preferred products of formula I are those wherein $R_6$ is quinolinium, isoquinolinium, 4-(methylthio)-pyridinium, thieno[2,3-b]-pyridinium, 1-methyl-pyrrolidinium, N-methyl-N-ethyl-N-(2-amino 2-oxoethyl)-aminium, imidazo (1,2-a)pyridinium or 6,7-diydro-5H-pyrindinium, those wherein $R_3$ and $R_4$ are both hydroxy and those wherein $R_2$ and $R_5$ are both chlorine or fluorine, those wherein $R_1$ and $R_2$ are both fluorine and those wherein $R_2$ is methoxy and one of $R_1$ or $R_5$ is chlorine.

Specific preferred compounds of formula I are:

the internal salt of (6R-(3-(E)6α,7β-(Z)))-1-(3-7-(((2-amino-4-thiazolyl)-(ethoxymethylphosphinyl-(3,4-dihydroxyphenyl)-methoxy)-imino)-acetamido)-2-carboxy-8-oxo-5-thia-1-azabicyclo[4,2,0]oct-2-en-3-yl) 2-propenyl)-quinolinium, the internal salt of (6R-(3-(E)6α,7β-(Z)))-7-(3-(7-(((2-amino-4-thiazolyl)-(ethoxymethylphosphinyl-(3,4-dihydroxyphenyl)-methoxy)-imino)-acetamido)-2-carboxy-8-oxo-5-thia-1-azabicyclo[4,2,0]oct-2-en-3-yl)-2-propenyl)-thieno(2,3-b)-pyridinium, the internal salt of (6R-(3-(E)6α,7β-(Z)))-7-(3-(7-((2-amino 4-thiazolyl)-(hydroxymethylphosphinyl-(3,4-dihydroxyphenyl)-methoxy)-imino)-acetamido)-2-carboxy-8-oxo-5-thia-1-azabicyclo[4,2,0]oct-2-en-3-yl)-2-propenyl)-thieno-(2,3-b)-pyridinium, the internal salt of (6R-(3-(E)6α,7β-(Z)))-7-(3-(7-(((2-amino-4-thiazolyl)-((2,5-dichloro 3,4-dihydroxyphenyl)-(diethoxyphosphinyl-methoxy)-imino)-acetamido)-2-carboxy-8-oxo-5-thia-1-azabicyclo[4,2,0]oct-2-en-3-yl)-2-propenyl)-thieno(2,3-b)pyridinium, the internal salt of (6R-(3-(E)6α,7β-(Z)))-7-(3-(7-(((2-amino 4-thiazolyl)-((2,5-dichloro-3,4-dihydroxyphenyl)-phosphonomethoxy)-imino)-acetamido)-2-carboxy-8-oxo 5-thia-1-azabicyclo[4,2,0]oct-2-en-3-yl)-2-propenyl)-thieno-(2,3-b)-pyridinium, the internal salt of (6R-(3(E),6α,7β(Z)))7-(3-(7-(((2-amino 4-thiazolyl)-(diethoxyphosphinyl-(3,4-dihydroxyphenyl)-methoxy)-imino)-acetamido)-2-carboxy-8-oxo-5-thia-1-azabicyclo[4,2,0]oct-2-en-3-yl)-2-propenyl)-thieno(2,3-b)-pyridinium, the internal salt of (6R-(3(E),6α,7β(Z)))7-(3-(7-(((2-amino 4-thiazolyl)-(3,4-dihydroxyphenyl)-phosphonomethoxy)-imino)-acetamido)-2-carboxy 8-oxo-5-thia-1-azabicyclo[4,2,0]oct-2-en-3-yl)-2-propenyl)-thieno(2,3-b)-pyridinium, the internal salt of (6R-(3(E),6α,7β(Z)))7-(3-(7-(((2-amino 4-thiazolyl)-((ethoxymethylphosphinyl)-(2,5-dichloro 3,4-dihydroxyphenyl)-methoxy)-imino)-acetamido)-2-carboxy-8-oxo 5-thia-1-azabicyclo[4,2,0]oct-2-en-3-yl)-2-propenyl)-thieno-(2,3-b)pyridinium (isomer A) and (isomer B), the internal salt of (6R-(3(E),6α,7β(Z)))7-(3-(7-(((2-amino 4-thiazolyl)-((hydroxymethylphosphinyl)-(2,5-dichloro-3,4-dihydroxyphenyl)-methoxy)-imino)-acetamido)-2-carboxy-8-oxo 5-thia-1-azabicyclo[4,2,0]oct-2-en-3-yl)2-propenyl)thieno(2,3-b)pyridinium, the internal salt of (6R-(3(E),6α,7β(Z)))1-(3-(7-(((2-amino 4-thiazolyl)-((ethoxymethylphosphinyl)-(2,5-dichloro-3,4-dihydroxyphenyl)-methoxy)-imino)-acetamido)-2-carboxy-8-oxo 5-thia-1-azabicyclo[4,2,0]oct-2-en-3-yl)-2-propenyl)-quinolinium (isomer A) and (isomer B), and the internal salt of (6R-(3(E),6α,7β(Z)))1-(3-(7-(((2-amino 4-thiazolyl)-((hydroxymethylphosphinyl)-(2,5-dichloro-3,4-dihydroxyphenyl)-methoxy)-imino)-acetamido)-2-carboxy-8-oxo 5-thia-1-azabicyclo[4,2,0]oct-2-en-3-yl)2-propenyl)-quinolinium.

The novel process of the invention for the preparation of a compound of formula I comprises reacting a compound of the formula

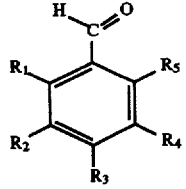

wherein $R_1$, $R_2$, $R_3$, $R_4$ and $R_5$ are as defined above optionally with any reactive functions protected to obtain an aromatic aldehyde of the formula

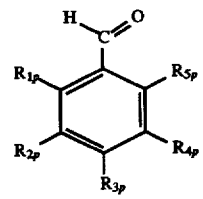

in which $R_{1p}$, $R_{2p}$, $R_{3p}$, $R_{4p}$ and $R_{5p}$ have the values of $R_1$, $R_2$, $R_3$, $R_4$ and $R_5$ as defined above optionally with a protected reactive function, reacting the latter with a reagent of the formula

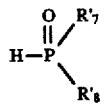

in which $R'_7$ is alkyl of 1 to 4 carbon atoms alkoxy of 1 to 4 carbon atoms or phenyl, $R'_8$ is alkoxy of 1 to 4 carbon atoms or $R'_7$ and $R'_8$ together form alkylenedioxy of 2 to 8 carbon atoms in the presence of a base to obtain a compound of the formula

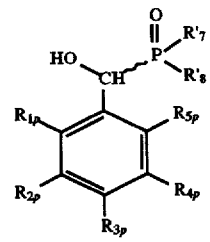

wherein $R'_7$ and $R'_8$ are defined as above and the wavy line symbolizes a mixture of isomers which optionally is separated, and which product of formula IV in the form of isomer A, isomer B or a mixture, is reacted with N-hydroxyphthalimide optionally in the presence of an activating agent to obtain a compound of the formula

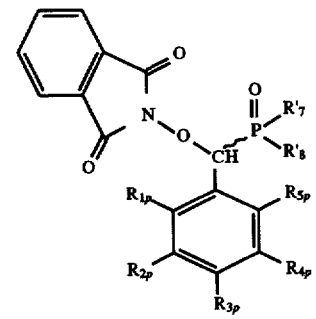

in the form of isomer A, isomer B or a mixture optionally hydrolyzed into an O-substituted hydroxylamine of the formula

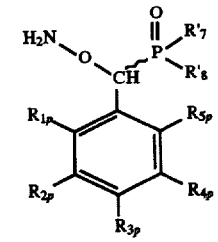

in the form of isomer A, isomer B or a mixture, condensing with a compound of the formula

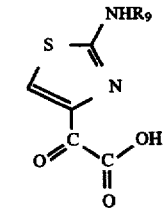

wherein $R_9$ is hydrogen or a protector group of the amine function to form a syn compound of the formula

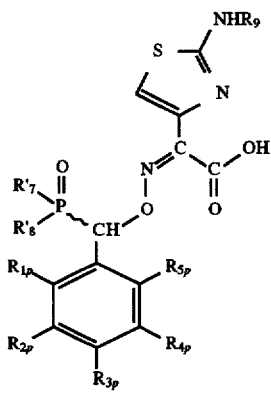

VIII in the form of isomer A, isomer B or a mixture, a functional derivative of which is optionally prepared and a product of formula VIII or a functional derivative thereof is amidified with an ester of the formula

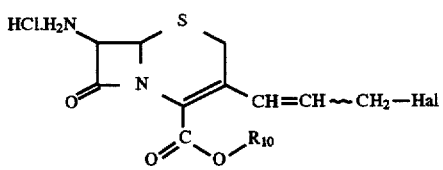

IX or its salts, wherein $R_{10}$ is the remainder of an easily cleavable ester to produce a compound of the formula

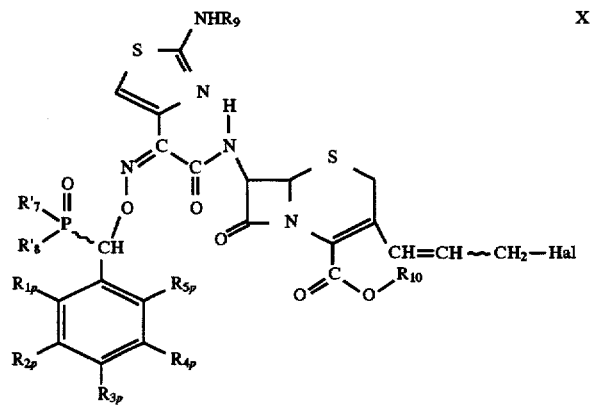

X in the form of isomer A, isomer B or a mixture, optionally converting the latter into a 3-(3-iodo propenyl) analog of the formula

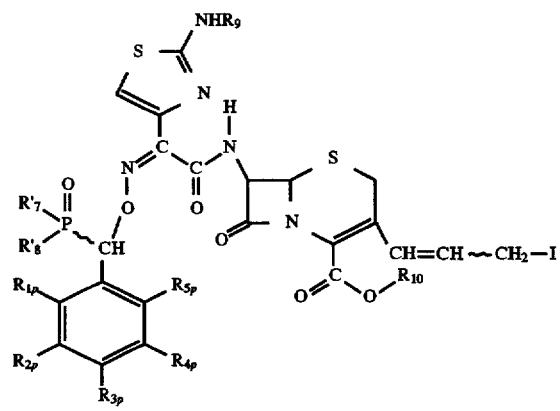

XI in the form of isomer A, isomer B or a mixture, reacting the latter with a base of formula $R_6$ to obtain a compound of the formula

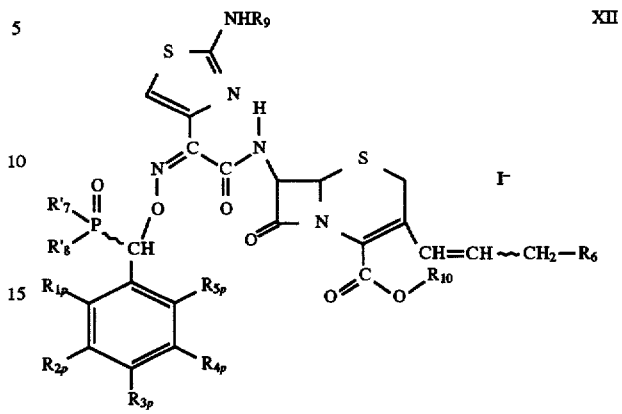

XII in the form of isomer A, isomer B or a mixture, optionally separating the (E) or (Z) isomers or converting the (Z) isomer into an (E) isomer and optionally subjecting it to one or more of the following reactions, in any appropriate order:

a) cutting by hydrolysis or by the action of thiourea of all or part of the ester groups or protection groups of the amino or of hydroxyls, b) dealkylation of one or two alkoxy groups carried by the phosphorus atom, c) esterification or salification by a base of the carboxylic(s) and salification by a base of the hydroxy(s) carried by the phosphorus atom, d) salification by an acid of the amino, and/or, e) separation of the products in the form of an R,S mixture into R and S.

In a variant of the process, the O-substituted hydroxylamine of formula VI is condensed with a compound of the formula

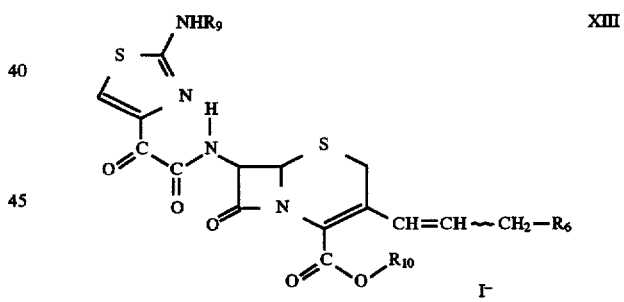

XIII produce the product of formula XII as defined previously.

The protected hydroxy functions of $R_{1p}$, $R_{2p}$, $R_{3p}$, $R_{4p}$ and $R_{5p}$, are selected from acyloxy groups such as formyloxy, acetoxy, propionyloxy, chloroacetoxy, bromoacetoxy, dichloroacetoxy, trichloroacetoxy, trifluoroacetoxy, methoxyacetoxy, phenoxyacetoxy, benzoyloxy, benzoylformyloxy, p-nitro benzoyloxy. The following groups can also be mentioned: ethoxycarbonyloxy, methoxycarbonyloxy, propoxycarbonyloxy, 2,2,2-trichloroethoxycarbonyloxy, allyloxycarbonyloxy, trimethylsilyl-ethoxycarbonyloxy, benzyloxycarbonyloxy, tert-butoxycarbonyloxy, 1-cyclopropyl ethoxycarbonyloxy, phthaloyloxy, butyryloxy, isobutyryloxy, valeryloxy, isovaleryloxy, oxalyloxy, succinyloxy and pivaloyloxy, phenylacetoxy, phenylpropionyloxy, mesyloxy, chlorobenzoyloxy, para-nitrobenzoyloxy, paratert-butyl benzoyloxy, caprylyloxy, acryloyloxy, methylcarbamoyloxy, phenylcarbamoyloxy and naphthylcarbamoyloxy.

Also can be mentioned are phenoxy, 4-chloro phenoxy, tolyloxy or tert-butyl phenoxy, tolylsulphonyloxy, tetrahydropyrannyloxy, tetrahydrothiopyrannyl oxy, methoxytetrahydropyrannyloxy, trityloxy, benzyloxy, 4-methoxy benzyloxy, benzhydryloxy, trichloro-ethoxy, 1-methyl 1-methoxyethoxy, alkoxy alkoxy-methoxy radicals such as methoxy ethoxy methoxy or trimethylsilylethoxymethoxy or trimethylsilylethoxy.

Two adjacent hydroxys can also be protected by forming a methylenedioxy, isopropylenedioxy, 1,1-cyclohexylbis (oxy), diphenylmethylenedioxy, carbonate or hydroxy borannylbis(oxy).

The protected hydroxy functions of $R_{1p}$, $R_{2p}$, $R_{3p}$, $R_{4p}$ and $R_{5p}$, are preferably selected from the following groups: methoxyethoxymethoxy, propionyloxymethoxy, acetoxymethoxy, butoxy, isobutoxy, tert-butoxy, pentoxy, hexyloxy, butyryloxymethoxy, valeryloxymethoxy, pivaloyloxymethoxy, 2-acetoxy ethoxy, 2-propionyloxy ethoxy, 2-butyryloxy ethoxy, 2-iodoethoxy, 2,2,2-trichloro ethoxy, vinyloxy, allyloxy, ethynyloxy, propynyloxy, benzyloxy, 4-methoxy benzyloxy, 4-nitro benzyloxy, phenylethoxy, trityloxy, diphenylmethyloxy or 3,4-dimethoxyphenoxy. 2-methoxy ethoxymethoxy (MEM-O) is particularly preferred.

The remainder of an easily cleavable ester of $R_{10}$ is chosen preferably from butyl, isobutyl, tert-butyl, pentyl, hexyl, methoxymethyl, ethoxymethyl, isopropyloxymethyl, α-methoxy ethyl, α-ethoxy ethyl, methylthiomethyl, ethylthiomethyl, isopropylthiomethyl, pivaloyloxymethyl, acetoxymethyl, propionyloxymethyl, butyryloxymethyl, isobutyryloxymethyl, valeryioxymethyl, isovaleryloxymethyl, tert-butylcarbonyloxymethyl, hexadecanoyloxymethyl, pivaloyloxymethyl, propionyloxyethyl, isovaleryloxyethyl, 1-acetoxy ethyl, 2-acetoxy ethyl, 1-propionyloxy ethyl, 2-propionyloxy ethyl, 1-butyryloxy ethyl, 2-butyryloxy ethyl, 1-(tert-butylcarbonyloxy)ethyl, 1-acetoxy propyl, 1-hexadecanoyloxy ethyl, 1-propionyloxy propyl, 1-methoxycarbonyloxy ethyl, methoxycarbonyloxymethyl, 1-acetoxy butyl, 1-acetoxy hexyl, 1-acetoxy heptyl, phthalidyl, 5,6-dimethoxy phthalidyl, tert-butylcarbonylmethyl, vinyl, allyl, 2-chloro allyl, etnynyl, propynyl, methoxycarbonylmethyl, benzyl, 4-methoxy benzyl, 4-nitro benzyl, phenethyl, trityl, diphenyl methyl, phenyl, 4-chloro phenyl, tolyl, tert-butyl phenyl, 3,4-dimethoxy phenyl, methoxyethoxymethyl, dimethylaminoethyl, cyanomethyl, tert-butoxycarbonylmethyl, 2,2-ethylenedioxy ethyl, cyanoethyl, 2,2-dimethoxy ethyl, 2-chloro ethoxymethyl, (2-hydroxy ethoxy)ethyl, 2,3-epoxy propyl, 3-dimethylamino 2-hydroxy propyl, 2-hydroxy ethyl, 2-methylaminoethoxymethyl, (2-amino ethoxy)methyl, 3-methoxy 2,4-thiadiazol-5-yl, tetrahydropyrann-2-yl, 1-methoxy 1-methyl ethyl, 2-hydroxy 1-methyl ethyl, isopropyl, carbamoylmethyl, chloromethyl, 2-chloro ethyl, 2,2,2-trichloro ethyl, 2-iodo ethyl, acetyl, methyl, 2-methylthio ethyl, thiocyanatomethyl, 2-chloro 1-acetoxy ethyl, 2-bromo 1-acetoxy ethyl, 2-fluoro 1-acetoxy ethyl, 2-methoxy 1-acetoxy ethyl, 2-methyl 1-acetoxy propyl, 1-methyl 1-acetoxy ethyl, 1-(methoxyacetoxy)ethyl, 1-acetyl carbonyloxyethyl, 1-hydroxy acetoxyethyl, 1-(2-thienyl)carbonyloxyethyl, 1-(2-furyl)carbonyloxyethyl, 1-(5-nitro 2-furyl)carbonyloxy-ethyl, 1-(2-pyrrolyl) carbonyloxyethyl, 1-(propionyloxy-carbonyloxy)ethyl, 1-(propoxycarbonyl-oxy)ethyl, 1-(isopropoxycarbonyloxy) ethyl, 1-(methoxyethoxycarbonyloxy)ethyl, 1-(allyloxycarbonyloxy)ethyl, isopropoxycarbonyl methyl, 1-[(2,3-epoxy propyl)oxycarbonyloxy]ethyl, 1-[(2-furyl) methoxycarbonyloxy]ethyl, 1-[(2-fluoro ethoxy) carbonyloxy]ethyl, 1-(methoxycarbonyloxy)propyl, 1-(methoxycarbonyloxy)1-methyl ethyl, (methoxycarbonyloxy)chloromethyl, 1-(methoxycarbonyloxy)2-chloro ethyl, 1-(methoxycarbonyloxy)2-methoxy ethyl, 1-(methoxycarbonyloxy)allyl or 5-methyl 2-oxo 1,3-dioxol-4-yl. Diphenylmethyl is more particularly preferred.

The protector group of the amino of $R_9$ can be for example carbamoyl, methylcarbamoyl, phenylcarbamoyl, naphthylcarbamoyl as well as the corresponding thiocarbamoyls, alkyl of 1 to 6 carbon atoms substituted or not substituted such as, preferably, trichloroethyl, tert-butyl or tert-amyl, aralkyl such as benzyl, 4-methoxy benzyl, phenethyl, trityl, 3,4-dimethoxy benzyl or benzhydryl, aliphatic, aromatic or heterocyclic acyl substituted or not, such as formyl, acetyl, propionyl, butyryl, isobutyryl, valeryl, isovaleryl, chloroacetyl, dichloroacetyl, trichloroacetyl, bromoacetyl, trifluoroacetyl benzoyl, toluolyl, naphthoyl, chlorobenzoyl, para-nitro benzoyl, para-tert-butyl benzoyl, phenoxyacetyl, caprylyl, decanoyl, acryloyl, phthaloyl, mesyl, phenylacetyl, phenylpropionyl, oxalyl, succinyl, pivaloyl, lower alkoxycarbonyl or cycloalkoxycarbonyl such as methoxycarbonyl, ethoxycarbonyl, propoxycarbonyl, 1-cyclopropylethoxycarbonyl, isopropoxycarbonyl, butoxycarbonyl, tert-butoxycarbonyl, pentoxycarbonyl, hexyloxycarbonyl, trichloroethoxy carbonyl, aralkoxycarbonyl such as benzyloxycarbonyl. Trityl is preferred.

The above list is not limitative and it is clear that other amine protector groups, groups known particularly in the chemistry of the peptides, can also be used.

The base in the presence of which the reagent of formula III is reacted can be an amine, particularly a tertiary amine such as triethylamine or pyridine or a slightly basic hydroxide such aluminum hydroxide or barium hydroxide, or an alkali metal carbonate or bicarbonate.

The activating agent in the presence of which the N-hydroxyphthalimide is reacted can be a phase transfer agent and such are known to one skilled in the art. The hydrolysis of the phthalimide of formula V is carried out by the action of hydrazine, preferably in the form of the hydrate.

The functional derivative of the acid of formula VIII can be for example a halide, a symmetrical or mixed anhydride, the amide, the azide or an activated ester. As an example of a mixed anhydride, there can be mentioned those formed with isobutyl chloroformate and that formed with pivaloyl chloride and the carboxylicsulfonic mixed anhydrides formed for example with p-toluene sulfonyl chloride. An example of an activated ester is the ester formed with 2,4-dinitrophenol and that formed with hydroxybenzothiazole.

Examples of a halide include chloride or the bromide. The anhydride can be formed in situ by the action of an N,N'-disubstituted carbodiimide, for example N,N-dicyclohexylcarbodiimide. The acylation reaction is preferably conducted in an organic solvent such as methylene chloride. Other solvents can be used such as tetrahydrofuran, chloroform or dimethylformamide.

When an acid halide is used and in a general manner when an acid molecule is released during the reaction, the reaction is preferably carried out in the presence of a base such as sodium hydroxide, potassium hydroxide, sodium or potassium carbonates and bicarbonates, sodium acetate, triethylamine, N,N-diisopropyl ethyl amine, pyridine, morpholine or N-methylmorpholine. The reaction temperature is generally lower than or equal to ambient temperature.

A product of formula VIII can also be made to react directly with a product of formula IX in the presence of a carbodiimide such as diisopropylcarbodiimide or 1-(3-dimethylamino propyl)3-ethyl carbodiimide (EDC). An example of one such preparation is given further on in the experimental part.

The action of reagents capable of introducing $R_6$ and producing the product of formula XII is carried out under the following conditions: When Hal is chlorine, a substitution of the chlorine by iodine can be carried out in situ or separately in the presence of sodium iodide and then the desired reagent is added in the optional presence of an organic solvent such as dichloromethane, acetonitrile, tetrahydrofuran, acetone or methylethylketone. The desired reagent of $R_6$ can also be reacted directly on the product of formula X or XI, in the presence of silver tetrafluoroborate.

The isomerism of the products of formula XII can be different from that of the products of formula X or XI. In the case where the Z isomer is isolated, this isomer can be converted into the E isomer by the usual methods, particularly by the action of iodine.

According to the values of $R_9$, $R_{10}$, $R_{1p}$, $R_{2p}$, $R_{3p}$, $R_{4p}$ and $R_{5p}$, the aim of the action on the product of formula XII of one or more hydrolysis, hydrogenolysis agents or thiourea is to eliminate $R_9$ when the latter is a protector group of the amino, to convert $R_{1p}$, $R_{2p}$, $R_{3p}$, $R_{4p}$ and $R_{5p}$ respectively into $R_1$, $R_2$, $R_3$, $R_4$ and $R_5$ when these carry a protector group of the hydroxyl(s) and/or to eliminate $R_{10}$ when this is an easily cleavable ester, one of those which it is desired to eliminate.

However, it is of course possible to eliminate $R_9$ and to convert $R_{1p}$, $R_{2p}$, $R_{3p}$, $R_{4p}$ and $R_{5p}$ respectively into $R_1$, $R_2$, $R_3$, $R_4$ and $R_5$ when these carry a protector group of the hydroxyl(s) without affecting $R_{10}$ when this must be preserved. The nature of the reagents to be used in such a case is well known to one skilled in the art. For example, a description of the different methods of eliminating the different protector groups will be found in French Patent No. 2,499,995. Examples of such reactions are given further on in the experimental part.

Given the nature of the preferred protector groups which are used: trityl for $R_9$, 2-methoxy-ethoxy-methyl to protect the hydroxy functions and 4-methoxy benzyl for $R_{10}$, trifluoroacetic acid is preferably used without a solvent or in a solvent such as anisole or a mixture of solvents such as anisole/methylene chloride. Then a salt is obtained with trifluoroacetic acid and the free base can be obtained by the action of a base such as a carbonate or triethylamine.

The optional partial or total dealkylation of the alkoxy(s) carried by the phosphorus atom is preferably carried out under moderate conditions. The operation is preferably carried out by the action of a trialkyl silyl halide, particularly trimethylsilyl bromide or iodide and the silylated intermediate obtained is hydrolyzed by the action of an alcohol, for example methanol or ethanol. The operation can also be carried out by the action of lithium bromide. The dealkylation is preferably carried out at the last stage, that is after elimination of the various protector groups. If appropriate, this does not have to be the case. The choice of the order of the reactions is within the capability of one skilled in the art.

The salification of the products can be carried out by the usual methods; it can for example be obtained by the action on a product in acid form or on a solvate, for example the ethanolic solvate, or a hydrate of this acid, of a mineral base such as sodium or potassium hydroxide, sodium or potassium carbonate or bicarbonate. The salts of mineral acids such as trisodium phosphate can also be used. Organic acid salts can be used such as sodium salts of saturated or unsaturated, linear or branched aliphatic carboxylic acids having 1 to 18 and preferably 2 to 10 carbon atoms. The aliphatic chains of these acids can be interrupted by one or more heteroatoms such as oxygen or sulfur or substituted by aryl such as phenyl, thienyl or furyl, by one or more hydroxyls or by one or more halogens such as fluorine, chlorine or bromine, preferably chlorine, by one or more carboxylic or lower alkoxycarbonyls, preferably methoxycarbonyl, ethoxycarbonyl or propyloxycarbonyl, by one or more aryloxys, preferably phenoxy.

Moreover, there can be used as organic acids, sufficiently soluble aromatic acids such as benzoic acid, substituted preferably by lower alkyl.

Examples of such organic acids are formic acid, acetic acid, acrylic acid, butyric acid, adipic acid, isobutyric acid, n-caproic acid, isocaproic acid, chloropropionic acid, crotonic acid, phenyl-acetic acid, (2-thienyl)-acetic acid, (3-thienyl)-acetic acid, (4-ethyl-phenyl)-acetic acid, glutaric acid, the monoethylic ester of adipic acid, hexanoic acid, heptanoic acid, decanoic acid, oleic acid, stearic acid, palmitic acid, 3-hydroxy-propionic acid, 3-methoxy-propionic acid, 3-methyl-thiobutyric acid, 4-chlorobutyric acid, 4-phenyl butyric acid, 3-phenoxy butyric acid, 4-ethylbenzoic acid, and 1-propyl benzoic acid.

However, sodium acetate, sodium 2-ethyl hexanoate or sodium diethyl acetate are preferably used as sodium salts. The salification can also be obtained by the action of an organic base such as triethylamine, diethylamine, trimethylamine, propylamine, N,N-dimethyl ethanolamine, tris[(hydroxymethyl)amino]methane, methylamine, ethanolamine, pyridine, picoline, dicyclohexyl amine, morpholine and benzylamine. It can also be obtained by the action of arginine, lysine, procaine, histidine, N-methyl glucamine.

This salification is preferably carried out in a solvent or a mixture of solvents such as water, ethyl ether, methanol, ethanol or acetone. The salts are obtained in amorphous or crystallized form according to the reaction conditions employed. The crystallized salts are preferably prepared by reacting the free acids with one of the salts of the aliphatic carboxylic acids mentioned above. The salification of the products by mineral or organic acids is carried out under the usual conditions.

The optional esterification of the products is carried out under standard conditions, generally by reacting the acid of formula I or a functional derivative with a derivative of formula:

$$Z-Re$$

in which Z is hydroxyl or halogen such as chlorine, bromine, iodine and Re is the ester group to be introduced, a non-exhaustive list of which group is given above. In some cases, it may be advantageous to carry out an esterification on a product the amine and/or reactional groups of which present on the oxyimino are blocked before removing the protector group of the amine and of the reactional group present on the oxyimino.

The products of formula I contain several asymmetrical carbons. In the cephem nucleus which contains two asymmetrical carbons, the two carbons are in R configuration. Furthermore, the group present on the oxyimino function also contains an asymmetrical carbon which can be in the R or S form or in the form of an R+S mixture. The separation of the two diastereoisomers can be carried out by means known to one skilled in the art, for example by chromatography.

The novel intermediates of the invention are those of formulae IV, V, VI, VIII, X, XI and XII.

The novel anti-bacterial compositions of the invention are comprised of an antibactericidally effective amount of a compound of formula I or its salts and an inert pharmaceutical carrier. The compositions may be in the form of tablets, dragees, capsules, granules, suppositories, ointments, creams, gels and injectable solutions or suspensions.

Examples of suitable pharmaceutical carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions possess a very good antibiotic activity on gram$^⊕$ bacteria such as staphylococci, streptococci and notably on penicillin-resistant staphylococci. Their effectiveness on enterobacteria which produce chromosomal or plasmid beta-lactamases is particularly remarkable. These properties make the compositions useful as medicaments in the treatment of infections caused by susceptible germs and notably in that of staphylococcia such as staphylococcal septicemia, malignant staphylococcia of the face or skin, pyodermatitis, septic or suppurating wounds, anthrax, phlegmohs, erysipelas, primary or post-influenzal acute staphylococcia, broncho-pneumonia, pulmonary suppurations. The compositions may also be useful for treatment of colibacilloses and associated infections, of infections caused by proteus, by klebsiella and by salmonella and of other illnesses caused by gram$^⊖$ bacteria.

The compositions can particularly be presented in the form of a powder intended to be dissolved extemporaneously in an appropriate vehicle, for example, apyrogenic sterile water as well as disinfectants for surgical instruments.

The novel method of the invention for combatting bacterial infections in warm-blooded animals, including humans, comprises administering to warm-blooded animals an antibiotically effective amount of at least one compound of formula I and its salts. The compounds may be administered orally, rectally, parenterally or topically on the skin and mucous membranes. A cleavable ester is preferred for oral administration. The usual daily dose is 3 to 50 mg/kg depending on the condition treated, the specific compound and the method of administration.

The products of formula II are generally known and are in the main commercially available; others can be prepared from commercially available products by methods described in European Application No. 0,551,034. For the preparation of the products of formula II, the methods described in the literature can also be used, particularly the so-called Rosemund reduction, the reduction of benzoic acids, or the formulation of aromatic rings such as the Vilsmeier-Haack reaction, the Gatterman-Koch reaction, the Reimer-Tiemann reaction or the reaction with formyl fluoride (J. Am. Chem. Soc., Vol. 82, p. 2380 (1960)).

The products of formulae VII and IX are also known in the literature, notably in Belgian Patent Application No. 864,828 and the European Patent Application No. 0,333,154. The preparation of the products of formula XIII is described in the European Application No. 0,551,034. The reagent of formula III can be prepared as described, for example, in Derwent 81.82015 D/45 Series C.

In the following examples, there are described several preferred embodiments to illustrate the invention. However, it should be understood that the invention is not intended to be limited to the specific embodiments.

EXAMPLE 1

Internal salt of (6R(3-(E),6α,7β(Z)))1-(3-(7-(((2-amino-4-thiazolyl)-(ethoxymethylphosphinyl(3,4-dihydroxyphenyl)-methoxy)-imino)-amino)-2-carboxy-8-oxo 5-thia 1-azabicyclo(4.2.0)oct-2-en-3-yl)-2-propenyl)-quinolinium STAGE A:
ethyl(hydroxy-(3,4-bis(2-methoxyethoxy)-methoxy)-benzyl)-methylphosphinate A solution of 9 g of 3,4-bis-[(methoxyethoxy)-methoxy]-benzaldehyde, 3.26 g of methyl-ethyl phosphite reagent prepared below and 7.97 ml of triethylamine was stirred for 24 hours at 75° C. and the triethylamine was evaporated under reduced pressure. The residue was purified on silica eluting with ethyl acetate, then with an ethyl acetate/ethanol system 95-5, 90-10, then 85-15 to obtain 6.85 g of the expected product with a $R_f$=0.2 (eluant AcOEt/EtOH 95-5).
Preparation of the methyl-ethyl phosphite reagent.

A solution of 25 g of dichloromethyl phosphine in 150 ml of ether was cooled to 0° C. and then 30 ml of triethylamine and 30 ml of ethanol dissolved in 40 ml of ether were added dropwise over 45 minutes. The mixture was stirred for 19 hours at ambient temperature and the triethylamine hydrochloride was eliminated by filtration, followed by rinsing with ether and evaporation of the solvents. After distillation of the residue under reduced pressure of 13 mbars, 12.9 g of reagent were obtained between 56° and 58° C. and had a $R_f$=0.2 (AcOEt-EtOH 95-5).

STAGE B:
ethyl((3,4-bis((2-methoxyethoxy)-methoxy)-phenyl)-((1,3-dihydro-1,3-dioxo-2H-isoindol-2-yl)-oxy)-methyl)-methylphosphinate 8.17 g of triphenyl phosphine and 2.8 g of N-hydroxyphthalimide were added to 6.59 g of the product of Stage A dissolved in 400 ml of tetrahydrofuran and the reaction mixture was cooled to 0°/-5° C. 5.43 g of diethyl azadicarboxylate were added and the mixture was stirred for 3 hours while allowing the reaction medium to return to ambient temperature. 150 ml of water were added and extraction was carried out with dichloromethane. The extracts were dried and the solvent was evaporated under reduced pressure. Purification was carried out by chromatography on silica (eluant: ethyl acetate, then ethyl acetate/ethanol 95-5) to obtain 1.32 g of the expected product with a $R_f$=0.35 (AcOEt/EtOH 95-5).

NMR spectrum (300 MHz CDCl$_3$ ppm)
1.34 P—O—CH$_2$—CH$_3$
1.68–1.77 —P—CH$_3$
3.55–3.87 and 5.29 O-MEM
4.0 to 4.3 P—O—CH$_2$—CH$_3$
5.55–5.67 CH~P—
7.17–7.53 phenyl
7.72 phthalimide STAGE C:
ethyl aminooxy-(3,4-bis(2-methoxyethoxy)-methoxy)-benzyl)-methylphosphinate 1.34 g of hydrazine hydrate were added to 4.62 g of the product of Stage B dissolved in 120 ml of ethanol and the mixture was stirred for one hour at ambient temperature. Filtration was carried out and the solvent was evaporated under reduced pressure to obtain 3.16 g of the expected product with a $R_f$=0.1 (AcOEt/EtOH 95-5).

NMR spectrum (CDCl$_3$ 250 MHz ppm)
1.28 —P—O—CH$_2$—CH$_3$
1.43–1.44 —P—CH$_3$
3.35–3.38–3.56–3.86 and 5.32 OMEM
3.8 to 4.3 —P—O—CH$_2$—CH$_3$
4.84 —CH~P—
6.9 to 7.25 aromatics.

STAGE D:
(Z)α-((ethoxymethylphosphinyl)-(3,4-((2-methoxyethoxy)-methoxy)-phenyl)-methoxy)-(2-((triphenyl-methyl)-amino)-4-thiazoleacetic acid.

2.95 g of the product of Stage C dissolved in 60 ml of methanol and 2.94 g of oxo-[2-[(triphenylmethyl)-amino]-thiazol-4-yl]acetic acid (described in the Belgian Patent Application No. 864,828) were stirred for 3 hours at ambient temperature. The solvent was evaporated under reduced pressure and purification was carried out by chromatography on silica (eluant: dichloromethane/methanol 90-10, then 80-20) to obtain 4.43 g of the expected product with a $R_f$=0.55 ($CH_2Cl_2$/MeOH 8-2).
NMR spectrum ($CDCl_3$ ppm)
1.03 —P—O—$CH_2$—$\underline{CH_3}$
1.20–1.57 —P—$CH_3$
3.27–3.34–3.51–3.8–4.12 and 5.2 to 5.52 —OMEM
3.51–3.8–4.12 —P—O—$\underline{CH_2}$—$CH_3$
5.2 to 5.52 —CH–P—
6.64 $H_5$ of the thiazole
6.9 to 7.23 aromatics.

STAGE E:

4-methoxy-benzyl[6R(3(E),6α,7β(Z))]-3-(3-chloro-1-propenyl)-7-(((((ethoxymethylphosphinyl)-(3,4-bis((2-methoxyethoxy)-methoxy)-phenyl)-methoxy)-imino)-(2-((triphenylmethyl)-amino)-4-thiazolyl)-acetamido)-8-oxo-5-thia-azabicyclo(4.2.0)-oct-2-ene-2-carboxylate 2.24 g of 4-methoxybenzyl 7β-amino-3-[(Z)-3-chloro-1-propenyl]-8-oxo-5-thia-1-azabicyclo[4.2.0]oct-2-ene-2-carboxylate hydrochloride (described in European Patent Application No. 0,333,154) were added to a solution of 4.3 g of the acid of Stage D in 200 ml of dichloromethane and then the reaction medium was cooled to −5° C. 1.29 g of dimethylamino-propyl-ethyl-carbodiimide (EDC) were added and the mixture was stirred at −5°/0° C. for 3 hours. 50 ml of phosphate buffer pH 7 were added and extraction was carried out with dichloromethane, then with ethyl acetate. The extracts were dried and the solvent was evaporated under reduced pressure. After purification on silica (eluant: dichloromethane-acetone (8-2)), 3.92 g of the expected product with a $R_f$=0.35 ($CH_2Cl_2$-acetone 7-3) were obtained.

STAGE F:

4-methoxy-benzyl[6R(3(E),6α,7β(Z))]3-(3-iodo 1-propenyl)-7-(((((ethoxymethylphosphinyl)-(3,4-bis((2-methoxyethoxy)-methoxy)-phenyl)-methoxy)-imino)-(2-(triphenylmethyl)-amino)-4-thiazolyl)-acetamido)-8-oxo-5-thia-1-azabicyclo(4.2.0)oct-2-ene-2-carboxylate 973 mg of sodium iodide were added to 1.96 g of the chlorinated product of Step E dissolved in 15 ml of acetone and the mixture was stirred for 35 minutes at ambient temperature. The solvent was evaporated under reduced pressure and the residue was poured into a 10% aqueous solution of sodium thiosulfate, followed by drying. The solvent was evaporated and the residue was purified on silica (eluant: dichloromethane-acetone 7-3, under nitrogen pressure) to obtain 1.56 g of the expected product.

STAGE G:

1-(3-(7-(((((ethoxymethylphosphinyl)-(3,4-bis((2-methoxyethoxy)-methoxy)-phenyl)-methoxy)-imino)-(2-(triphenylmethyl)-amino)-4-thiazolyl)-acetamido)-2-(((4-methoxyphenyl)-methoxy)-carbonyl)-8-oxo-5-thia-1-azabicyclo(4.2.0)oct-2-en-3-yl)-2-propenyl)-quinolinium [6R(3(E),6α,7β(Z)]iodide 700 mg of the iodinated product of Stage F and 700 mg of quinoline were dissolved in 5 ml of dichloromethane and then the solvent was evaporated. The residue was stirred at ambient temperature for one hour and 20 ml of ether were added. The mixture was stirred for one hour and the precipitate was separated and rinsed with ether. After purification on silica (eluant: dichoromethane-methanol 95/5), 476 mg of the expected product were obtained with a $R_f$=0.35 ($CH_2Cl_2$-methanol 95-5).

NMR spectrum ($CDCl_3$ 300 MHz ppm)
1.1 to 1.29 —O—$CH_2$—$\underline{CH_3}$
1.54 —P—$CH_3$
3.01–3.06–3.38 $OCH_3$ of —OMEM
3.2 to 4.0 —O—$\underline{CH_2}$—$CH_3$ and $CH_2$ of OMEM and $CH_2S$
3.78 —Φ—O—$CH_3$
5.09 —O—CH—P—
6.0 to 6.14 —CH=CH—$\underline{CH_2}$
6.4 to 6.5 —CH=$\underline{CH}$—$CH_2$
6.7 $H_5$ of the thiazole
6.85 to 7.40 aromatics
7.96–8.14–8.27–8.38–9.0–10.33 quinoline.

STAGE H:

Internal salt of (6R(3-(E),6α,7β(Z)))1-(3-(7-(((2-amino-4-thiazolyl)-(ethoxymethylphosphinyl-(3,4-dihydroxyphenyl)-methoxy)-imino)-amino)-2-carboxy-8-oxo-5-thia-1-azabicyclo(4.2.0)oct-2-en-3-yl)-2-propenyl)-quinolinium 450 mg of the product of Stage G in 4 ml of trifluoroacetic acid with 10% anisole were stirred at ambient temperature for 3 hours and after 0.4 ml of water were added, the mixture was stirred for one hour. After filtration and rinsing with trifluoroacetic acid, 25 ml of ether were added at 0° C. The mixture was stirred for one hour, followed by separating, rinsing with ether and drying under reduced pressure for 16 hours at ambient temperature to obtain 255 mg of the expected product is obtained.

NMR spectrum ($CDCl_3$ 300 MHz ppm)
1.0 to 1.2 —O—$CH_2$—$\underline{CH_3}$
1.35–1.45 —P—$CH_3$
3.08 to 3.9 —O—$\underline{CH_2}$—$CH_3$
3.57–3.79 —S—$CH_2$
5.2 to 5.28 —O—CH—P—
5.8 to 5.95 —CH=CH—$\underline{CH_2}$
6.4 and 7.01 —CH=$\underline{CH}$—$CH_2$
6.67 to 6.79 $H_5$ of the thiazole+aromatics
7.31 $NH_2$
9.77 —NH—
8.07–8.26–8.51–8.52–9.34–9.59 quinoline.

EXAMPLE 2

Internal salt of (6R(3-(E),6α,7β-(Z)))7-(3-(7-((2-amino-4-thiazolyl)-(ethoxymethylphosphinyl-(3,4-dihydroxyphenyl)-methoxy)-imino)-acetamido)-2-carboxy-8-oxo-5-thia-1-azabicyclo(4.2.0)oct-2-en-3-yl)-2-propenyl)-thieno(2,3-b)pyridinium

STAGE A:

1-(3-(7-(((((ethoxymethylphosphinyl)(3,4-bis((2-methoxyethoxy)methoxy)phenyl)methoxy)imino)(2-((triphenylmethyl)amino)4-thiazolyl)acetyl)amino)2-(((4-methoxyphenyl)methoxy) carbonyl)8-oxo 5-thia 1-azabicyclo(4.2.0)oct2-en-3-yl)2-propenyl)thieno(2,3-b)-pyridinium[6R(3(E),6α,7β(Z))]iodide 837 mg of the iodinated derivative of Stage F of Example 1 and 608 mg of thieno-pyridine were dissolved in 5 ml of dichloromethane and then the solvent was evaporated. The residue was stirred at ambient temperature for one hour and after 20 ml of ether were added, the mixture was stirred for 30 minutes. The precipitate was separated and rinsed with ether. After purification on silica (eluant: dichoromethane-methanol 95/5), 693 mg of the expected product was obtained with a $R_f$=0.55 ($CH_2Cl_2$-methanol 80-20).

NMR spectrum ($CDCl_3$ 300 MHz ppm)
1.1 to 1.30 —O—$CH_2$—$\underline{CH_3}$
1.40 to 1.65 —P—$CH_3$
3.03 to 3.2–3.37 $OCH_3$ of —OMEM
3.28 to 4.2 —O—$\underline{CH_2}$—$CH_3$ and —O—$CH_2$—O— of OMEM and $CH_3S$
3.8 —Φ—O—$CH_3$
5.1 to 5.35 —O—$CH_2$—O— and $CO_2$—$CH_2$—o
5.6 to 5.9 —CH=CH—$\underline{CH_2}$ and —O—CH—P
6.25 to 6.5 —CH=$\underline{CH}$—$CH_2$
6.72 $H_5$ of the thiazole
6.88 to 7.40 aromatics
7.5 to 9.65 thienopyridine.

STAGE B:

Internal salt of (6R(3-(E),6α,7β(Z)))7-(3-(7-((2-amino-4-thiazolyl)-(ethoxymethylphosphinyl-(3,4-dihydroxyphenyl)-methoxy)-imino)-acetamido)-2-carboxy-8-oxo-5-thia-1-azabicyclo(4.2.0)-oct-2-en-3-yl)-2-propenyl)-thieno(2,3-b)pyridinium 693 mg of the product of Stage A in 6 ml of trifluoroacetic acid with 10% anisole were stirred at ambient temperature for 3 hours, and after 0.5 ml of water was added, the mixture was stirred for one hour. After filtration and rinsing with trifluoroacetic acid, 25 ml of ether were added at 0° C., and the mixture was stirred for 45 minutes, followed by separating, rinsing with ether and drying under reduced pressure for 16 hours at ambient temperature to obtain 343 mg of the expected product.

NMR spectrum (CDCl$_3$ 300 MHz ppm).
1.09 to 1.15 and 1.36–1.46 —O—CH$_2$—CH$_3$ and —P—CH$_3$
3.6 to 4.01 —S—CH$_2$ and —O—CH$_2$—CH$_3$
5.25 —O—CH—P
5.68 —CH=CH—CH$_2$
6.33 —CH=CH—CH$_2$—
6.68 to 6.80 H$_5$ of the thiazole+aromatics
7.83–8.27–8.16–9.09–9.24 thienopyridine.

EXAMPLE 3

Internal salt of (6R(3-(E),6α,7β(Z)))7-(3-(7-((2-amino-4-thiazolyl)-((hydroxymethylphosphinyl-(3,4-dihydroxyphenyl)-methoxy)-imino)-acetamido)-2-carboxy-8-oxo-5-thia-1-azabicyclo(4.2.0)oct-2-en-3-yl)-2-propenyl)-thieno(2,3-b)pyridinium 495 mg of N-methyl-N-(trimethylsilyl)-trifluoroacetamide (MSTFA) were added to 274 mg of the product of Example 2 suspended in 10 ml of dichloromethane, and the mixture was stirred for 10 minutes at ambient temperature. 427 mg of trimethylsilyl iodide were added and then the mixture was stirred for 2 hours at ambient temperature. 2 ml of tetrahydrofuran were added and the reaction medium was stirred for one hour at ambient temperature to eliminate the excess trimethylsilyl iodide. Then, the solvent was evaporated and the residue was taken up in 8 ml of acetone with 10% methanol. The suspension was stirred for 2 hours, followed by separating, rinsing with ether and drying under reduced pressure for 16 hours at ambient temperature to obtain 215 mg of the expected product.

NMR spectrum (CDCl$_3$ 300 MHz ppm)
1.32 —P—CH$_3$
3.5 to 3.9 —S—CH$_2$
5.06 —O—CH—P
6.31 and 7.15 CH=CH—CH$_2$
6.5 to 6.9 H$_5$ of the thiazole+aromatics
9.76 NH
7.88–8.28–8.14–9.08–9.22 thienopyridine.

EXAMPLE 4

Internal salt of (6R(3-(E),6α,7β(Z)))7-(3-(7-(((2-amino-4-thiazolyl)-((2,5-dichloro-3,4-dihydroxyphenyl)-(diethoxyphosphinyl)-methoxy)-imino)-acetamido)-2-carboxy-8-oxo-5-thia-1-azabicyclo(4.2.0)oct-2-en-3-yl)-2-propenyl)-thieno(2,3-b)pyridinium

STAGE A:

ethyl(hydroxy-(2,5-dichloro-3,4-bis((2-methoxyethoxy)-methoxy)-benzyl)ethoxyphosphinate 1.15 g of 2,5-dichloro-3,4-bis[(2-methoxy ethoxy)-methoxy]-benzaldehyde prepared as indicated in European Patent Application No. 0,551,034 were stirred for 3 hours at ambient temperature with 0.42 g of diethylphosphite and 2 g of alumina. The mixture was taken up in dichloromethane, filtered and the solvent was evaporated under reduced pressure. After purification on silica (eluant: dichloromethane-ethyl acetate 5-5), 1.13 g of the expected product were obtained with a R$_f$=0.15 (CH$_2$Cl$_2$-AcOEt 7-3).

STAGE B:

ethyl((2,5-dichloro-3,4-bis((2-methoxyethoxy)-methoxy)-phenyl)-((1,3-dihydro-1,3-dioxo-2H-isoindol-2-yl)-oxy)-methyl)-ethoxyphosphinate 421 mg of the product oF Stage A, 2 ml of toluene, 393 mg of triphenyl phosphine and 179 mg of N-hydroxyphthalimide were mixed together under an inert atmosphere and after the suspension was cooled to 0° C., 0.23 ml of diethyl azodicarboxylate were added. The reaction mixture was stirred for one hour at 0° C., then for 2 hours at ambient temperature. A few ml of water were added, followed by extraction with ethyl acetate, washing with water, drying and evaporating the solvents under reduced pressure to obtain 0.85 g of crude product which was purified on silica (eluant: dichloromethane-ethyl acetate 7-3) to obtain 310 mg of the expected product with a R$_f$=0.3 (CH$_2$Cl$_2$-AcOEt 7-3).

NMR spectrum (CDCl$_3$ 300 MHZ ppm)
1.3–1.4 and 4.1 to 4.4 P—(OEt)$_2$
3.3 and 3.37 CH$_3$ of OMEM
3.5 to 3.6–3.9 to 4.05 —O—CH$_2$—CH$_2$—O of OMEM
5.18–5.25 —O—CH$_2$—O of OMEM
6.25 —CH–P
8.01 phenyl CH
7.65 to 7.80 phthalimide.

STAGE C:

ethyl(aminooxy-((2,5-dichloro-3,4-bis(2-methoxyethoxy)-methoxy)-benzyl-ethoxyphosphinate 0.50 g of hydrazine hydrate were added to 6 g of the product of Stage B dissolved in 60 ml of ethanol and the mixture was stirred for one hour at ambient temperature. After filtration, the solvent was evaporated under reduced pressure and the residue was taken up in a few ml of dichloromethane, followed by filtration. The solvent was evaporated to obtain 3.9 g of the expected with a R$_f$=0.15 (CH$_2$Cl$_2$-AcOEt 6-4).

NMR spectrum (CDCl$_3$ 300 MHz ppm)
1.28–1.32 and 4.0 to 4.25 P—(O—CH$_2$—CH$_3$)$_2$
3.38 and 3.39–3.59 and 4.00 and 5.25 and 5.27 OMEM
3.8 to 4.3 —P—O—CH$_2$—CH$_3$
5.47 (d, J=15.5) —CH–P 7.45 aromatics.

STAGE D:

(Z)α-((diethoxyphosphinyl)(2,5-dichloro-3,4-((2-methoxy-ethoxy)-methoxy)-phenyl)-methoxy)-imino)-2-((triphenylmethyl)-amino)-4-thiazoleacetic acid.

544 mg of the product of Stage C dissolved in 5 ml of methanol and 570 mg of oxo-[2-[(triphenylmethyl)-amino]-thiazol-4-yl]acetic acid (described in Belgian Patent Application No. 864,828) were stirred for one hour at ambient temperature. The solvent was evaporated under reduced pressure and purification was carried out by chromatography on silica (eluant: ethyl acetate/ethanol 7-3) to obtain 520 mg of the expected product with a R$_f$=0.2 (AcOEt/EtOH 7-3).

NMR spectrum (CDCl$_3$ 300 MHz ppm)
1.16–1.26 and 4.10 —P—(O—CH$_2$—CH$_3$)$_2$
3.35–3.36 CH$_3$ of OMEM
3.57–3.97 CH$_2$ of OMEM
5.22 (d, J=16.5) —CH–P—
6.70 H$_5$ of the thiazole
7.92 aromatics.

STAGE E:

4-methoxy-benzyl-[6R(3(E),6α,7β(Z))]-3-(3-chloro-1-propenyl)-7-((((2,5-dichloro-3,4-bis-((2-methoxyethoxy)- methoxy)phenyl)-(diethoxyphosphinyl)-methoxy)-imino)-(2-((triphenylmethyl)amino)-4-thiazolyl)-acetyl)-amino)-8-oxo-5-thia-1-azabicyclo(4.2.0)oct-2-ene-2carboxylate 1.57 g of 4-methoxy-benzyl 7β-amino-3-[(Z)-3-chloro-1-propenyl]-8-oxo-5-thia-1-azabicyclo[4.2.0]oct-2-ene 2-carboxylate hydrochloride (described in European Patent Application No. 0,333,154) were added to a solution of 3.1 g of the acid of Stage D in 60 ml of dichloromethane and the reaction mixture was cooled to 0° C. 763 mg of dimethylamino propyl-ethyl-carbodiimide (EDC) were added and the mixture was stirred at 0° C. for one hour. The reaction mixture was taken up in dichloromethane, then washed with a phosphate buffer solution pH 7 and dried. The solvent was evaporated under reduced pressure and after purification by chromatography on silica (eluant: dichloromethane-ether (85-15)), 1.42 g of the expected product were obtained with a $R_f$=0.2 ($CH_2Cl_2$-AcOEt 8-2).

NMR spectrum ($CDCl_3$ 300 MHz ppm)
1.09–1.31–3.98–4.18 —P—(O—$CH_2$—$CH_3$)$_2$
3.44 $CH_2$—S—
3.37 $CH_3$ of OMEM
3.58 and 5.25 $CH_2$ of O-MEM
3.81 methoxybenzyl
5.77–6.32 —CH=CH—$CH_2$Cl
6.21 —CH~P—
6.81 to 6.94 tritylamino
7.30–7.62 aromatics.

STAGE F:

4-methoxy-benzyl[6R(3(E),-6α,-7β(Z))]-3-(3-iodo-1-propenyl)-7-((((diethoxyphosphinyl)-2,5dichloro-(3,4-bis((2-methoxyethoxy)-methoxy)-phenyl)-methoxy)-imino)-(2-((triphenylmethyl)-amino)-4-thiazolyl)-acetamido)-8-oxo-5-thia-1-azabicyclo(4.2.0)-oct-2-ene-2-carboxylate 168 mg of sodium iodide and one crystal of iodine were added to 360 mg of the chlorinated product of Stage E dissolved in 2 ml of acetone and the mixture was stirred for one hour at ambient temperature. The solvent was evaporated under reduced pressure and the residue was taken up in dichloromethane, washed with a 10% aqueous solution of sodium thiosulfate and dried. The solvent was evaporated to obtain 312 mg of the expected product.

STAGE G:

7-(3-(7-((((2,5-dichloro-3,4-bis((2-methoxyethoxy)-methoxy)-phenyl)-(diethoxyphosphinyl)-methoxy)-imino)-(2-((triphenylmethyl)-amino)-4-thiazolyl)-acetamido)-2-(((4methoxyphenyl)-methoxy)-carbonyl)-8-oxo-5-thia-1-azabicyclo(4.2.0)oct-2-en-3-yl)-2-propenyl)-thieno(2,3-b)-pyridinium-[6R(3(E),-6α,-7β(Z)]iodide.

260 mg of the iodinated derivative of Stage F and 240 mg of thienopyridine were stirred for one hour at ambient temperature. Precipitation took place by the addition of ether, followed by separating and drying under reduced pressure at ambient temperature. Chromatography was carried out on silica (eluant: dichloromethane-methanol 95-5) to obtain 110 mg of the expected product with a $R_f$=0.25 ($CH_2Cl_2$-MeOH 9-1).

NMR spectrum ($CDCl_3$ 400 MHz ppm)
1.07–1.12–1.25 to 1.28–3.69 —P—(O—$CH_2$—$CH_3$)$_2$
3.36–3.37 $OCH_3$ of —OMEM
3.23 to 3.28 and 3.57–3.97 $CH_2$ of OMEM
3.80 and 6.9 to 7.38 —Φ—O—$CH_3$
4.16 —$CH_2$—S—
6.20 —O—CH—P—
6.44 —CH=C̱H̱—$CH_2$—
6.76–6.80 $H_5$ of the thiazole
7.28 and 7.54–7.60 trityl NH
7.68–7.87–8.06–8.82–8.98 thienopyridine
8.57 CO—NH.

STAGE H:

Internal salt of (6R(3-(E),6α,7β(Z)))7-(3-(7-((2-amino 4-thiazolyl)-(((2,5-dichloro-3,4-dihydroxy-phenyl)-(diethoxyphosphinyl)-methoxy)-imino)-acetamido)-2-carboxy-8-oxo-5-thia-1-azabicyclo(4.2.0)oct-2-en-3-yl)-2-propenyl)-thieno(2,3-b)-pyridinium 100 mg of the product of Stage G in 1 ml of trifluoroacetic acid with 10% anisole were stirred at ambient temperature for 2 hours. After filtration and rinsing with trifluoroacetic acid, the filtrate was precipitated by the addition of ether. After separating, washing with ether and drying under reduced pressure, 43 mg of the expected product were obtained.

NMR spectrum ($CDCl_3$ 400 MHz ppm)
1.28 and 3.93 to 4.10 P—(O—$CH_2$—$CH_3$)$_2$
3.60 to 3.80 —S—$CH_2$
5.76 —CH—P—
5.67 —CH=CH—C̱H̱$_2$—$N^+$
6.31 —CH=C̱H̱—$CH_2$—$N^+$
6.76 $H_5$ thiazole
7.02 dichlorinated aryl
7.15 —C̱H̱=CH—$CH_2$—$N^+$
7.88–8.14–8.27–9.08–9.22 thieno pyridine.

EXAMPLE 5

Internal salt of (6R(3-(E),6α,7β(Z)))-7-(3-(7-(((2-amino-4-thiazolyl)-(((2,5-dichloro-3,4-dihydroxyphenyl)-phosphonomethoxy)-imino)-acetamido)-2-carboxy-8-oxo-5-thia-1-azabicyclo (4.2.0)oct-2-en-3-yl)-2-propenyl)-thieno(2,3-b) pyridinium 0.21 ml of N-methyl-N-(trimethylsilyl)-trifluoroacetamide (MSTFA) were added to 190 mg of the product of Example 4 in suspension in 4 ml of dichloromethane, and the mixture was stirred for 5 minutes at ambient temperature. 0.3 ml of trimethylsilyl iodide was added and then the mixture was stirred for 2 hours at ambient temperature. 2 ml of tetrahydrofuran were added and the mixture was stirred for 15 minutes at ambient temperature to eliminate excess trimethylsilyl iodide. Then, the solvent was evaporated and the residue was taken up in 3 ml of acetone with 10% methanol. The mixture was stirred for 45 minutes at ambient temperature and the solvent was evaporated under reduced pressure. The product was solidified by the addition of ether and after filtration, washing with ether and drying under reduced pressure, 123 mg of the expected product were obtained.

NMR spectrum (DMSO 400 MHz ppm)
5.70 to 5.85 —O—CH—P
5.67 CH=CH—C̱H̱$_2$
6.33 CH—C̱H̱—$CH_2$
6.77 $H_5$ of the thiazole
7.11 to 7.15 C̱H̱=CH—$CH_2$ and chlorophenyl
7.89 and 8.28–8.15–9.09–9.22 thienopyridine
9.61 and 9.71 NH.

EXAMPLE 6

Internal salt of (6R(3-(E),6α,7β(Z))7-(3-(7-(((2-amino-4-thiazolyl)-((diethoxyphosphinyl)-3,4-dihydroxyphenyl)-methoxy)-imino)-acetamido)-2-carboxy-8-oxo-5-thia-1-azabicyclo(4.2.0)oct-2-en-3-yl)-2-propenyl-thieno(2,3-b)pyridinium

STAGE A:

ethyl(hydroxy-(3,4-bis(2-methoxyethoxy)-methoxy)-phenyl)-methyl)-ethoxyphosphinate 30 g of alumina were added at ambient temperature to 15.7 g of 3,4-bis[(2-methoxyethoxy)-methoxy]- benzaldehyde dissolved in 6.9 g of diethylphosphite and the reaction mixture stood for 2 hours at ambient temperature. Filtration was carried out, followed by washing with dichloromethane. The solvent was evaporated under reduced pressure to obtain 21 g of crude product which was chromatographed on silica (eluant: dichloromethane, then ethyl acetate-ethanol 9-1) to obtain 19.4 g of the expected product with a $R_f$=0.25 (AcOEt-EtOH 9-1).

STAGE B:

ethyl((3,4-bis((2-methoxyethoxy)-methoxy)-phenyl)-((1, 3-dihydro-1,3-dioxo-2H-isoindol-2-yl)-oxy)-methyl)-ethoxyphosphinate 12 g of the product of Stage A, 240 ml of tetrahydrofuran, 10.35 g of triphenylphosphine and 4.76 g of N-hydroxyphthalimide were mixed together under an inert atmosphere and the solution was cooled to 0° C. 6.2 ml of diethyl azadicarboxylate in 10 ml of tetrahydrofuran were added and the mixture was stirred for 30 minutes at 0° C., then for 30 minutes at ambient temperature. 100 ml of water were added and extraction was carried out with ethyl acetate. The extracts were washed with water, dried and the solvents were evaporated under reduced pressure. The remaining product stood for 16 hours at +4° C. and the crystals formed were separated and washed in ether. The solvent was evaporated from the filtrate and the residue was chromatographed on silica (eluant: ethyl acetate, then ethyl acetate-ethanol 95-5) to obtain 6.8 g of the expected product with a $R_f$=0.3 (AcOEt-EtOH 9-1).

NMR spectrum (CDCl$_3$ 250 MHz ppm)
1.33–1.37 and 4.25 —P—(OET)$_2$
3.34–3.36 the CH$_3$'s of OMEM
3.55–3.88 the CH$_2$'s of OMEM
5.8 —CH~P—
7.10 to 7.8 aromatics.

STAGE C:

ethyl(aminooxy-(3,4-bis(2-methoxyethoxy)-methoxy)-benzyl-ethoxyphosphinate 6.8 g of the product of Stage B, 100 ml of ethanol and 0.95 ml of hydrazine hydrate were stirred for one hour at 60° C. The reaction medium was cooled, filtered, followed by washing with ethanol and evaporating the solvent under reduced pressure. The residue was chromatographed on silica (eluant: ethyl acetate-ethanol 95-5) to obtain 3.9 g of the expected product with a $R_f$=0.15 (AcOEt-EtOH 95-5).

NMR spectrum (CDCl$_3$ 250 MHz ppm)
1.25–1.30 and 4.10 —P—(OEt)$_2$
3.36–3.38 CH$_3$ of OMEM
3.56–3.85 (CH$_2$)$_2$ of OMEM
4.89 —CH~P—
5.32 O—CH$_2$—O of OMEM
7.06 and 7.2 to 7.3 aromatics.

STAGE D:

1-(3-(7-(((((diethoxyphosphinyl)-(3,4-bis((2-methoxyethoxy)-methoxy)-phenyl)-methoxy)-imino)-(2-((triphenylmethyl)-amino)-4-thiazolyl)-acetamido)-2-(((4-methoxyphenyl)-methoxy)-carbonyl)-8-oxo-5-thia-1-azabicyclo(4.2.0)oct2-en-3-yl)-2-propenyl)-quinolinium-[6R(3(E),-6α,-7β(Z)]-iodide 373 mg of the product of Stage C and 650 mg of 1-(3-(7-((hydroxy-imino)-(2-(triphenylmethyl)-amino)-4-thiazolyl)-acetamido)-2-(((4-methoxyphenyl)-methoxy)-carbonyl)-8-oxo-5-thia-1-azabicyclo(4.2.0)oct-2-en-3-yl)2-propenyl)-quinolinium[6R(3(E),6α,7β(Z)]iodide were dissolved in 6 ml of dichloromethane and 20 ml of methanol and 150 mg of p-toluene sulfonic acid were added. The mixture was stirred for 16 hours at ambient temperature and another 100 mg of the product of Stage C were added. The mixture was stirred for 6 hours at ambient temperature and the solvent was evaporated under reduced pressure. The residue was taken up in ether and dried under reduced pressure to obtain 905 mg of crude product which was used as is for the following stage.

STAGE E:

Internal salt of (6R(3-(E),6α,7β(Z))-7-(3-(7-(((2-amino-4-thiazolyl)-((diethoxyphosphinyl)-3,4-dihydroxyphenyl)-methoxy)-imino)-acetamido)-2-carboxy-8-oxo-5-thia-1-azabicyclo(4.2.0)oct-2-en-3-yl)-2-propenyl)-thieno(2,3-b) pyridinium 900 mg of the product of Stage D were mixed at ambient temperature with 9 ml of trifluoroacetic acid with 10% anisole and then, 0.9 ml of dichloromethane were added with stirring for 2 hours. The solvent was evaporated under reduced pressure and ether was added. The precipitate was separated, washed with ether and dried. It was taken up again in 7 ml of trifluoroacetic acid with 15% water and 0.6 ml of dichloromethane and the mixture was stirred for 2 hours, followed by filtration. The solvent was evaporated under reduced pressure, followed by precipitation with ether, separating and drying to obtain 519 mg of the expected product with a $R_f$=0.3 (acetone-water 7-3).

NMR spectrum (DMSO 300 MHz ppm)
1.05 to 1.20 and 3.45 to 4.0 —P—(OEt)$_2$.

EXAMPLE 7

Internal salt of (6R(3-(E),6α,7β(Z)))7-(3-(7-(((2-amino-4-thiazolyl)-(3,4-dihydroxyphenyl)-phosphonomethoxy)-imino)-acetamido)-2-carboxy-8-oxo-5-thia-1-azabicyclo(4.2.0)oct-2-en-3-yl)-2-propenyl)-thieno(2,3-b)-pyridinium 0.5 ml of N-methyl-N-(trimethylsilyl)-trifluoroacetamide (MSTFA) were added to 500 mg of the product of Example 6 in suspension in 10 ml of dichloromethane and the mixture was stirred for 5 minutes at ambient temperature. 1 ml of trimethysilyl iodide was added and stirring was continued for 2 hours at ambient temperature. 2.5 ml of tetrahydrofuran were added and the mixture was stirred for one hour at ambient temperature to eliminate excess trimethylsilyl iodide. Then, the solvent was evaporated and the residue was taken up in 10 ml of acetone with 10% methanol. The suspension was stirred for 2 hours, followed by separating, rinsing with dichloromethane, then with ethanol and drying under reduced pressure at ambient temperature to obtain 296 mg of the expected product.

NMR spectrum (CDCl$_3$ 300 MHZ ppm)
1.32 —P—CH$_3$
3.61 to 3.77 —S—CH$_2$
5.11 —O—CH—P
5.67–6.31 and 7.18 CH=CH—CH$_2$—
6.6 to 6.9 H$_5$ of the thiazole+aromatics
7.89–8.26–8.15–9.08–9.23 thienopyridine.

EXAMPLE 8

Internal salt of (6R(3-(E),6α,7β(Z))) 7-(3-(7-(((2-amino-4-thiazolyl)-(((ethoxymethylphosphinyl)-(2, 5-dichloro-(3,4-dihydroxyphenyl)-methoxy)-imino)-acetamido)-2-carboxy-8-oxo-5-thia-1-azabicyclo (4.2.0)oct-2-en-3yl)-2-propenyl)-thieno(2,3-b)-pyridinium (isomer A)

Stage A:

ethyl(hydroxy-2,5-dichloro-3,4-bis((2-methoxyethoxy)-methoxy)-benzyl-methyl phosphinate 29.97 g of 2,5-dichloro 3,4-bis((methoxyethoxy)-methoxy-benzaldehyde prepared as in European Patent Application No. 0,551,034 and 6.8 g of methylethylphosphite reagent prepared as in Stage A of Example 1 were heated at 70° C. for 70 minutes in the presence of 16.68 ml of triethylamine and the triethylamine was eliminated under reduced pressure to obtain 30.5 g of the expected product which was purified by chromatography on silica (eluant: AcOEt-EtOH 98-2) to obtain the product with a R$_f$=approx. 0.35 (AcOEt-EtOH 98-2).

Stage B:

ethyl((2,5-dichloro-3,4-bis((2-methoxyethoxy)-methoxy)-phenyl)-((1,3-dihydro-1,3-dioxo-2H-isoindol-2-yl)-oxy)-methyl)-methylphosphinate (isomer A and isomer B).

Using the procedure of Stage B of Example 1, 18.4 g of the product of Stage A, 6.72 g of hydroxy phthalimide, 14.72 g of triphenylphosphine and 8.89 ml of diethylazodicarboxyl were reacted and by carrying out the extraction with ethyl acetate, 50 g of crude product were obtained which was purified by chromatography on silica (eluant: AcOEt-hexane 9-1) to obtain 7.23 g of isomer A with a R$_f$=0.45 (AcOEt-hexane 9-1) and 8.78 g of isomer B with a R$_f$=0.40 (AcOEt-hexane 9-1).

NMR spectrum (CDCl$_3$ 300 MHz ppm)
1.28 and 3.90 to 4.22 P—(OEt)
1.81 P—(CH$_3$)
3.33 and 3.57 CH$_3$ of OMEM
3.55–3.98 O—CH$_2$—CH$_2$—O of OMEM
5.19–5.25 —O—CH$_2$—O of OMEM
6.27 —CH~P
8.00 phenyl CH
7.77 phthalimide.

Stage C:

ethyl(aminooxy-((2,5-dichloro-3,4-bis(2-methoxyethoxy)-methoxy)-benzyl-methyl)-methylphosphinate (isomer-A).

7.2 g of the product of Stage B (isomer A) in 60 ml of dichloromethane were cooled to 0° C. and 0.824 ml of hydrazine hydrate were added. The mixture was stirred for 90 minutes and after filtration, the solvent was evaporated under reduced pressure. The residue was chromatographed on silica (eluant: AcOEt-EtOH 95-5) to obtain 5.29 g of the expected product with a R$_f$=0.20 (AcOEt-EtOH 95-5).

NMR spectrum (CDCl$_3$ 300 MHz ppm)
1.24 and 3.83 to 4.16 P—(OEt)
1.54 (d, J=14.5) P—(CH$_3$)
3.38 and 3.39–3.58 and 4.01 and 5.26 and 5.27 OMEM
5.41 (d, J=9.5) —CH~P
5.78 NH$_2$
7.41 aromatics.

Stage D:

(Z)α-(methylethoxyphosphinyl)-(2,5-dichloro-3,4-((2-ethoxyethoxy)-methoxy)-phenyl)-methoxy)-imino)-(2-((triphenylmethyl)-amino)-4-thiazole-acetic-acid (isomer A).

Using the procedure of Stage D of Example 1, 4 g of the oxyamine of Stage C and 3.60 g of oxo (2-((triphenylmethyl)-amino)-thiazol-4-yl)acetic acid (described in Belgian Patent Application No. 864,828 were reacted to obtain 7.40 g of crude product which was chromatographed on silica (eluant: CH$_2$Cl$_2$-MeOH 95-5, then 90-10) to obtain 5.69 g of the expected product with a R$_f$=0.5 (CH$_2$Cl$_2$-Me—OH 85-15).

NMR spectrum (CDCl$_3$ 300 MHz ppm)
1.03 CH$_3$ of P—(OEt)
1.63 P—(CH$_3$)
3.45–3.50 CH$_3$ of OMEM
3.54–3.64–3.79–3.95 CH$_2$ of P—(OEt) and of O—(CH$_2$)$_2$—O 5.20 O—CH$_2$—O 6.55 H$_5$ thiazole 7.20–7.53 aromatics.

Stage E:

4-methoxy-benzyl-(6R(3(E),-6α,-7β(Z)))-3-(3-chloro-1-propenyl)-7-(((((2,5-dichloro-3,4-bis-((2-methoxyethoxy)-methoxy)-phenyl)-(methylethoxy-phosphinyl)-methoxy)-imino)-2-(triphenylmethyl)-amino)-4-thiazolyl)-acetamido)-8-oxo-5-thia-1-azabicyclo(4.2.0)-oct-2-en-2carboxylate (isomer A).

Using the procedure of Example 1, Stage E, 5.60 g of the product of Stage D and 2.68 g of 4-methoxy-benzyl 7β-amino 3-((Z)3-chloro-1-propenyl)-8-oxo-5-thia-1-azabicyclo(4.2.0)oct-2-en-2-carboxylate hydrochloride (described in European Patent Application No. 0,333,154) and 1.43 g of dimethylaminopropyl-ethyl carbodiimide (EDC) were reacted to obtain 7.56 g of crude product which was purified by chromatography on silica (eluant: CH$_2$Cl$_2$-acetone 85-15) to obtain the desired product with a R$_f$=0.3 (CH$_2$Cl$_2$-acetone 85-15).

NMR spectrum (CDCl$_3$ 300 MHz ppm)
1.00–1.10 P—(O—CH$_2$—CH$_3$)
3.44 CH$_2$—S—
3.37 CH$_3$ of OMEM
3.40 to 4 (CH$_2$)$_2$ of O—MEM and CH$_2$—Cl
3.81 methoxybenzyl
5.12 to 5.38 O—CH$_2$—O
6.31 —CH=CH—CH$_2$Cl
6.15 to 6.18 —CH~P—
7.30 tritylamino
7.30–7.61 aromatics.

Stage F:

4-methoxy-benzyl(6R(3(E),6α,7β(Z)))-3-(3-iodo-1-propenyl)-7-(((((2,5-dichloro-3,4-bis((2-methoxyethoxy)-methoxy)-phenyl)-(methylethoxyphosphinyl)-methoxy)-imino)-2-(triphenylmethyl)-amino)-4-thiazolyl)-acetamido)-8-oxo-5-thia-1-azabicyclo(4.2.0)oct-2-en-2carboxylate (isomer A).

Using the procedure of Stage F of Example 1, 1.47 g of the product of Stage E and 690 mg of sodium iodide were reacted to obtain after chromatography on silica (eluant: CH$_2$Cl$_2$-acetone 80-20), 1.42 g of the expected product which was used as is for the following stage.

NMR spectrum (CDCl$_3$ 300 MHz ppm)
1.00–1.09 and 3.99 P—(OEt)
1.65 to 1.71 and 3.47 P—CH$_3$ and S—CH$_2$—
3.37–3.38 O—CH$_3$ of OMEM
3.57–4.00 O—CH$_2$ of OMEM
3.82 Φ—OCH$_3$
5.10–5.25 O—CH$_2$—O of OMEM and Φ—CH$_2$—O
6.05 to 6.30 O—CH—P and I—CH$_2$—CH
6.79–6.82 H$_5$ thiazole
7.27 to 7.40 trityl NH.

Stage G:

7-(3-(7-(((((2,5-dichloro-3,4-bis((2-methoxyethoxy)-methoxy)-phenyl)-(methylethoxyphosphinyl)-methoxy)-imino-2-(triphenylmethyl)-amino)-4-thiazolyl)-acetamido)-2-(((4-methoxyphenyl)-methoxy)-carbonyl)-8-oxo-5-thia-1-azabicyclo(4.2.0)oct-2-en-3-yl)-2-propenyl)-thieno-(2,3-b)pyridinium-(6R(3(E),6α,7β(Z)))iodide (isomer A).

Using the procedure of Stage G of Example 4, the product of Stage F and 0.776 g of 2,3-b-thienopyridine were reacted to obtain after chromatography on silica (eluant: dichloromethane-methanol 90-10), 0.93 g of the expected product with a R$_f$=0.25 (CH$_2$Cl$_2$-MeOH 95-5).

NMR spectrum (CDCl$_3$ 300 MHz ppm)
0.99–1.09 and 3.57–3.98–3.40 to 4.00 P—(O—CH$_2$—CH$_3$)
1.65–1.70 P—CH$_3$
3.31–3.37 CH$_3$ of OMEM and CH$_2$—S
3.57–3.38 and 3.40 to 4.00 CH$_2$ of O-MEM 3.31–3.37 —Φ—O—CH₃
4.16 —CH₂—S—
5.63–5.79–5.99 CH₂ of the propenyl
6.13–6.16 —O—CH—P—
6.49 —CH=CH—CH₂—
6.78–6.80 H₅ of the thiazole
6.91 the NH's
7.30 trityl NH
7.51–7.60–7.65–7.88–8.06–8.82 thienopyridine.

Stage H:

Internal salt of (6R(3(E),6α,7β(Z)))7-(3(7-(((2-amino 4-thiazolyl)-((2,5-dichloro-3,4-dihydroxyphenyl)-(methylethoxyphosphinyl)-methoxy)-imino)-acetamido)-2-carboxy-8-oxo-5-thia-1-azabicyclo(4.2.0)oct-2-en-3-yl)-2-propenyl)-thieno-(2,3-b)pyridinium (isomer A).

Using the procedure of Stage H of Example 1, 880 mg of the product of Stage G and 9 ml of a solution of trifluoroacetic acid with 10% anisole were reacted to obtain 476 mg of the expected product.

NMR spectrum (CDCl₃ 400 MHz ppm)
1.16 to 3.97 P—(O—CH₂—CH₃)
1.48 P—CH₃
3.55 to 3.80 CH₂—S
5.68 —CH—P
5.68 —CH=CH—CH₂—N⁺
6.35 —CH=CH—CH₂—N⁺
6.75–6.77 H₅ of the thiazole
6.99 dichlorinated aryl
7.17 —CH=CH—CH₂—N⁺
7.30 NH₂
7.89–8.29–9.09–9.15–9.23 thienopyridine

EXAMPLE 9

Internal salt of (6R(3-(E),6α,7β(Z)))7-(3-(7-(((2-amino-4-thiazolyl)-((ethoxymethylphosphinyl)-(2,5-dihydro-(3,4-dihydroxyphenyl)-methoxy)-imino)-acetamido)-2-carboxy-8-oxo-5-thia-1-azabicyclo(4.2.0)oct-2-en-3-yl)-2-propenyl)-thieno(2,3-b)-pyridinium (isomer B)

Stage A:

ethyl(amino-oxy-((2,5-dichloro-3,4-bis-(2-methoxyethoxy)-methoxy)-benzyl)-methylphosphinate (isomer B).

Using the procedure of Stage C of Example 8, 9.5 g of isomer B of Stage B of Example 8 and 1.45 ml of hydrazine hydrate were reacted to obtain 6.70 g of the expected product melting at <50° C.

NMR spectrum (CDCl₃ 300 MHz ppm)
1.30–4.12 P—(OEt)
1.45 P—CH₃
3.60–4.01 O—CH₂—CH₂—O
5.27 O—CH₂—O
5.40 CH–P Stage B:

(Z)α-((ethoxymethylphosphinyl)-2,5-dichloro-(3,4-((2-methoxyethoxy)-methoxy)-phenyl)-methoxy)-2-((triphenylmethyl)-amino)-4-thiazole acetic acid (isomer B).

Using the procedure of Stage D of Example 1, 4 g of the product of Stage A and 3.60 g of the ketoacid derivative were reacted to obtain 7.14 g of the expected product with a R_f=0.50 (CH₂Cl₂-MeOH 85-15).

NMR spectrum (CDCl₃ 300 MHz ppm)
3.38 OCH₃ of OMEM
3.58–3.99–3.90 to 4.25 O—CH₂—CH₂—O—
5.23 O—CH₂—O
7.21 trityl
2.95 mobile 2H's
6.87 mobile 1H Stage C:

4-methoxy-benzyl(6R(3(E),6α,7β(Z)))3-(3-chloro-1-propenyl)-7-(((((ethoxymethyl-phosphinyl)-2,5-dichloro-3, 4-bis-((2-methoxyethoxy)-methoxy)-phenyl)-methoxy)-imino)-2-(triphenylmethyl)-amino)-4-thiazolyl)-acetamido) -8-oxo-5-thia-1-azabicyclo(4.2.0)oct-2-en-2-carboxylate (isomer B).

Using the procedure of Example 1 Stage E, 5.50 g of the product of Stage B and 2.63 g of 4-methoxy-benzyl 7β-amino-3-((Z)3-chloro-1-propenyl)-8-oxo-5-thia-1-azabicyclo(4.2.0)oct-2-en-2-carboxylate hydrochloride (described in European Patent Application No. 0,333,154) and 1.40 g of dimethylaminopropyl-ethyl carbodiimide (EDC) were reacted to obtain 7.32 g of crude product which was purified by chromatography on silica (eluant: CH₂Cl₂-acetone 85-15) to obtain the expected product with a R_f=0.3 (CH₂Cl₂-acetone 85-15).

NMR spectrum (CDCl₃ 300 MHz ppm)
1.27–1.42 CH₃ of P—(OEt) and P—CH₃
3.38 CH₃ of OMEM
3.70 to 3.99 CH₂—S
3.81 methoxybenzyl
3.98 to 3.99 (CH₂)₂ of OMEM
4.17 —CH=CH—CH₂Cl
5.15–6.32 —CH=CH—CH₂Cl
6.16–6.18 —CH–P—
6.78–6.84 thiazole H₅
7.30 tritylamino
6.88–7.30 aromatics
7.58 dichlorophenyl.

Stage D:

4-methoxy-benzyl(6R(3(E),6α,7β(Z)))-3-(3-iodo-1-propenyl)-7-(((((ethoxymethyl-phosphinyl)-2,5-dichloro-3, 4-bis-((2-methoxyethoxy)-methoxy)-phenyl)-methoxy)-imino)-2-(triphenylmethyl)-amino)-4-thiazolyl)-acetamido) -8-oxo-5-thia-1-azabicyclo-(4.2.0)oct-2-en-2-carboxylate (isomer B).

Using the procedure of Stage F of Example 1, 2.98 g of the product of Stage C and 1.40 g of sodium iodide were reacted to obtain 3.14 g of the expected product which was used as is for the following stage.

NMR spectrum (CDCl₃ 300 MHz ppm)
0.97–1.06 and 3.99 P—(OEt)
1.71 P—CH₃
3.57 O—CH₃ of OMEM
3.58 CH₂ of OMEM
3.82 Φ—OCH₃
5.25 O—CH₂—O of OMEM and Φ—CH₂—O
6.10 to 6.18 O—CH—P
6.77–6.80 H₅ thiazole
7.20 to 7.40 trityl NH.

Stage E:

7-(3-(7-(((((2,5-dichloro-3,4-bis-((2-methoxyethoxy)-methoxy)-phenyl)-(methyl ethoxyphosphinyl)-methoxy)-imino)-2-(triphenylmethyl)-amino)-4-thiazolyl)-acetamido) -2-(((4-methoxyphenyl)-methoxy)-carbonyl)-8-oxo-5-thia-1-azabicyclo(4.2.0)oct-2-en-3-yl)-2-propenyl)-thieno-(2,3-b)pyridinium-(6R(3(E),6α,7β(Z))iodide (isomer B).

Using the procedure of Stage G of Example 4, the product of Stage D and 1.57 g of 2,3-b-thienopyridine were reacted to obtain after chromatography on silica (eluant: dichloromethane-methanol 90-10), 1.92 g of the product with a R_f=0.25 (CH₂Cl₂-MeOH 95-5).

NMR spectrum (CDCl₃ 300 MHz ppm)
1.20 to 1.40 and 4.14 P—(OEt)
1.20 to 1.40 P—CH₃
3.31–3.37 CH₃ of OMEM and CH₂—S
3.57–3.99–3.66 O—CH₂—O and S—CH₂
3.37–3.38 —Φ—O—CH₃
5.25 O—CH₂—O 5.60 to 6.04 and 6.44 $N^+$—$CH_2$—CH
6.75–6.79 $H_5$ of the thiazole
6.90 to 7.40 trityl N and Φ—$CH_2$—O
7.50 to 7.53–7.70–7.87–8.06–8.83–9.97 thienopyridine.

Stage F:

Internal salt of (6R(3(E),6α,7β(Z)))-7-(3(7-(((2-amino-4-thiazolyl)-(((2,5-dichloro-3,4-dihydroxy-phenyl)-(methylethoxyphosphinyl)-methoxy)-imino)-acetamido)-2-carboxy-8-oxo-5-thia-1-azabicyclo(4.2.0)oct-2-en-3yl)-2-propenyl)-thieno-(2,3-b)pyridinium (isomer B).

Using the procedure of Stage H of Example 1, 1.9 g of the product of Stage G and 19 ml of a trifluoroacetic acid solution with 10% anisole were reacted to obtain 818 mg of the expected product.

NMR spectrum (CDCl$_3$ 400 MHz ppm)
1.15 and 3.55 to 4.10 P—(O—$CH_2$—$CH_3$)
1.53 P—$CH_3$
3.55 to 4.10 $CH_2$—S
5.68 —CH—P
5.68 —CH=CH—$CH_2$—$N^+$
6.34 —CH=$CH$—$CH_2$—$N^+$
6.76 $H_5$ of the thiazole
6.99 dichlorinated aryl
7.17 —$CH$=CH—$CH_2$—$N^+$
7.29 $NH_2$
7.89–8.10–8.28–9.08 thienopyridine

EXAMPLE 10

Internal salt of (6R(3-(E),6α,7β(Z)))7-(3-(7-(((2-amino-4-thiazolyl)-((hydroxymethylphosphinyl)-(2,5-dichloro-(3,4-dihydroxyphenyl)-methoxy)-imino)-acetamido)-2-carboxy-8-oxo-5-thia-1-azabioyclo (4.2.0)oct-2-en-3yl)-2-propenyl)-thieno(2,3-b) pyridinium 80 mg of the product of Example 8 and 88 μl of N-methyl-N-trimethylsilyl-trifluoroacetamide were mixed together under an inert atmosphere and the mixture was stirred for 5 minutes. 52 μl of trimethylsilyl iodide were added and the mixture was stirred for 2 hours at ambient temperature. 1.25 ml of tetrahydrofuran were added and the mixture was stirred for one hour. The solvent was evaporated under reduced pressure and the residue was taken up in ether. The mixture was stirred for 30 minutes followed by drying. A solution of ether with 10% of ethanol was added followed by stirring for 2 hours and filtration. The solvent was evaporated under reduced pressure to obtain 68 mg of the expected product.

NMR spectrum (CDCl$_3$ 300 MHz ppm)
1.43 P—$CH_3$
3.40 to 3.80 $CH_2$—S
5.60 —CH~P
5.63 —$CH$=CH—$CH_2$—$N^+$
6.33 —CH=$CH$—$CH_2$—$N^+$
6.74–6.76 $H_5$ of the thiazole
6.98 dichlorinated aryl
7.17 —$CH$=CH—$CH_2$—$N^+$
7.88–8.14–8.28–9.08–9.22 thienopyridine

EXAMPLE 11

Internal salt of (6R-(3(E),6α,7β(Z)))1-(3-(7-(((2-amino-4-thiazolyl)-((ethoxymethylphosphinyl)-(2,5-dichloro-3,4-dihydroxyphenyl)-methoxy)-imino)-acetamido)-2-carboxy-8-oxo-5-thia-1-azabicyclo[4,2,0]oct-2-en-3yl)-2-propenyl)-quinolinium (isomer A).

Stage A:

1-(3-(7-(((((ethoxymethylphosphinyl)-2,5-dichloro-(3,4-bis((2-methoxyethoxy)-methoxy)-phenyl)-methoxy)-imino) -(2-(triphenylmethyl)-amino)-4-thiazolyl)-acetamido)-2-(( (4-methoxyphenyl)-methoxy)-carbonyl)-8-oxo-5-thia-1-azabicyclo-(4.2.0)oct-2-en-3-yl)-2-propenyl)-quinolinium [6R(3(E),6α,7β(Z))]iodide (isomer A).

Using the procedure of Stage G of Example 4, 2.80 g of iodinated product of Example 8, Stage F, and 1.36 ml of quinoline were reacted to obtain 1.34 g of the expected product with a melting point of 150° C.

NMR spectrum (CDCl$_3$ 300 MHz ppm)
0.97–1.08 P—O—$CH_2$—$CH_3$
1.66 P—$CH_3$
3.57–3.98 P—O—$CH_2$—$CH_3$ and $CH_2$ of OMEM
3.30–3.37 $CH_3$ of OMEM
3.78–3.8 Φ—O—$CH_3$
5.76–5.98–6.25 $N^+$—$CH_2$—CH=CH and CH~P
6.46 —$CH$=CH—$CH_2$—$N^+$
6.76–6.79 thiazole $H_5$
7.25 to 7.38 trityl
7.50–7.59 dichloroaryl Stage B:

Internal salt of (6R-(3(E),6α,7β(Z)))1-(3-(7-(((2-amino-4-thiazolyl)-((ethoxymethylphosphinyl)-(2,5-dichloro-3,4-dihydroxyphenyl)-methoxy)-imino)-acetamido)-2-carboxy-8-oxo-5-thia-1-azabicyclo[4,2,0]oct-2-en-3yl)-2-propenyl)-quinolinium (isomer A).

Using the procedure of Stage H of Example 1, 1.4 g of the product of Stage A and 14 ml of trifluoroacetic acid with 10% anisole were reacted to obtain 750 mg of the expected product.

NMR spectrum (DMSO ppm)
1.15 P—O—$CH_2$—$CH_3$
1.48 P—$CH_3$
3.50 to 4.05 S—$CH_2$ and P—O—$CH_2$—$CH_3$
5.71 CH~P
6.42 to 6.98 $N^+$—$CH_2$—CH
6.76 thiazole $H_5$
6.98 dichloroaryl
7.36 $NH_2$
8.07–8.26–8.54–9.84 quinoline

EXAMPLE 12

Internal salt of (6R-(3(E),6α,7β(Z)))1-(3-(7-(((2-amino-4-thiazolyl)-((ethoxymethylphosphinyl)-(2,5-dichloro-3,4-dihydroxyphenyl)-methoxy)-imino)-acetamido)-2-carboxy-8-oxo-5-thia-1-azabicyclo[4,2,0]oct-2-en-3yl)-2-propenyl)-quinolinium (isomer B).

Stage A:

1-(3-(7-(((((ethoxymethylphosphinyl)-2,5-dichloro-(3,4-bis((2-methoxyethoxy)-methoxy)-phenyl)-methoxy)-imino) -(2-(triphenylmethyl)-amino)-4-thiazolyl)-acetamido)-2-(((4 methoxyphenyl)-methoxy)-carbonyl)-8-oxo-5-thia-1-azabicyclo4.2.0)oct-2-en-3-yl)-2-propenyl)-quinolinium[6R (3(E),-6α,7β(Z)]-iodide (isomer B).

Using the procedure of Stage G of Example 4, 1.55 g of iodinated product prepared as indicated in Example 9, Stage D and 0.695 ml of quinoline were reacted to obtain 0.695 g of the expected product.

NMR spectrum (DMSO ppm)
1.27 and 4.13 P—OEt
1.27–1.36 P—$CH_3$
3.37 $CH_3$ of OMEM
3.57–3.97–4.13 O—$CH_2$—$CH_2$—O of OMEM and S—$CH_2$
5.23 O—$CH_2$—O of OMEM
5.77–5.97–6.16 CH~P and $N^+$—$CH_2$
6.47 $N^+$—$CH_2$—$CH$
6.74–6.79 thiazole $H_5$ 6.89–7.37 Φ—CH₂—O
7.29 trityl
7.97–8.10 to 8.30–8.38–8.98–10.41 quinoline
Stage B:

Internal salt of (6R-(3(E),6α,7β(Z)))1-(3-(7-(((2-amino-4-thiazolyl)-(((ethoxymethylphosphinyl)-(2,5-dichloro-3,4-dihydroxyphenyl)-methoxy)-imino)-acetamido)-2-carboxy-8-oxo-5-thia-1-azabicyclo[4,2,0]oct-2-en-3yl)-2-propenyl)-quinolinium (isomer B).

Using the procedure of Stage H of Example 1, 0.750 g of the product of Stage A and 8 ml of trifluoroacetic acid with 10% anisole were reacted to obtain 539 mg of the expected product.
NMR spectrum (DMSO ppm)
1.13–1.15 —CH₃ of P—(OEt)
1.53 P—CH₃
3.70 to 4.0 CH₂ of P—(OEt)
3.50 to 3.8 S—CH₂
5.68 CH–P
5.88 N⁺—CH₂
6.41 N⁺—CH₂—CH
6.74–6.77 thiazole H₅
6.98 dichloroaryl
7.30 NH₂
8.07–8.22 to 8.31–8.53–9.34 quinoline

EXAMPLE 13

Internal salt of (6R-(3(E),6α,7β(Z)))1-(3-(7-(((2-amino-4-thiazolyl)-(((hydroxymethynlphosphinyl)-(2,5-dichloro-3,4-dihydroxyphenyl)-methoxy)-imino)-acetamido)-2-carboxy-8-oxo-5-thia-1-azabicyclo[4,2,0]oct-2-en-3yl)-2-propenyl)-quinolinium.

Using the procedure of Example 10, 80 mg of the product of Example 11 or 12 or their mixture, 88 μl of N-methyl-N-trimethylsilyl-trifluoroacetamide and then 52 μl of trimethylsilyl iodide were reacted to obtain 68 mg of the expected product.
NMR spectrum (CDCl₃ ppm)
1.00 P—CH₃
3.59 to 3.79 S—CH₂
5.62 O—CH—P
6.41 N⁺—CH₂—CH
6.79 thiazole H₅
6.95 to 7.20 dichloroaryl and N⁺—CH₂—CH=CH
8.27–8.53–8.07–9.58 quinoline In addition to the products described above in the examples, the products corresponding to the formula below and resulting from the combinations of the different values of the substituents represented in the tables which follow, constitute products which can be obtained according to the invention.

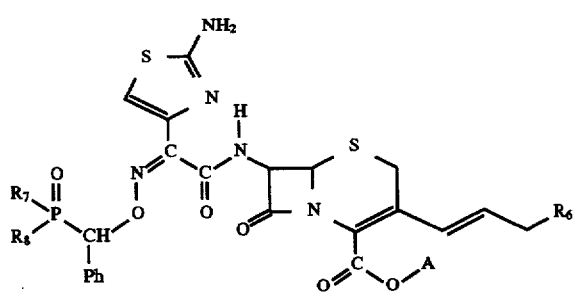

In these products, R₇/R₈ are OH/OH, OEt/OEt, CH₃/OH and CH₃/OEt.

| Ph | R₆ | R₇ | R₈ |
|---|---|---|---|
| (2,4-difluoro-3-hydroxy-phenyl with OH) | pyrrolidinyl-F⁻ | OH | OH |
| (trifluoro-dihydroxyphenyl) | benzothiazol-amidine-N⁻ | OEt | OEt |
| | pyridinium-N⁻ | CH3 | |
| (difluoro-dihydroxyphenyl) | thiazolyl-N⁻ | | |
| | pyridinyl-S—CH₃-N⁻ | | |
| (CF₃-dihydroxyphenyl) | | | |
| (Cl, CF₃-dihydroxyphenyl) | thiazolopyridinyl-amidine-N⁻ | | |
| (F, F-OCH₃-dihydroxyphenyl) | benzothiophene-N⁻ | | |
| (Cl, OCH₃-dihydroxyphenyl) | benzimidazolyl-N—CH₃-X⁻ | OH | OH |
| (Cl-dihydroxyphenyl) | thiazolo-imidazolyl-N⁻ | OEt | OEt |

-continued

| Ph | R6 | R7 | R8 |
|---|---|---|---|
|  | 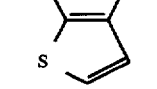 | | CH3 |
| 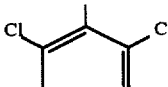 | 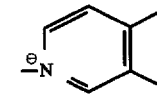 | | |
| 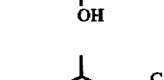 |  | | |
| 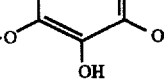 | 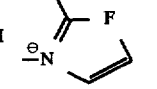 | | |
| 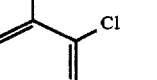 |  | OH | OH |
| 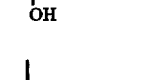 |  | OEt | OEt |
| 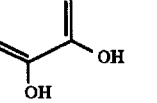 | 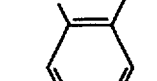 | | CH3 |
| | 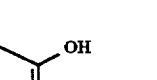 | | |
| | 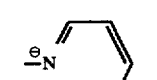 | | |

EXAMPLE 14

Preparations were produced for injection of 500 mg of the product of Example 4 and 5 ml of sterile aqueous excipient s.q.f. to 5 ml.

PHARMACOLOGICAL STUDY OF THE PRODUCTS OF THE INVENTION

Activity in vitro, method of dilutions in liquid medium.

A series of tubes was prepared into which an equal amount of sterile nutritive medium was divided and increasing quantities of the product to be studied was distributed into each tube. Then, each tube was seeded with a bacterial strain and after incubation for twenty-four hours in an oven at 37° C., the growth inhibition was evaluated by transillumination which allowed the minimal inhibiting concentrations (M.I.C.) expressed in µg/ml to be determined (TABLE I).

Activity in vitro, method of dilutions in solid medium.

A series of dishes was prepared into which an equal amount of sterile nutritive medium was distributed, containing increasing amounts of the product to be studied and then each dish was seeded with several bacterial strains. After incubation for 24 hours in an oven at 37° C., the growth inhibition was evaluated by the absence of any bacterial development which allowed the minimal inhibiting concentrations (M.I.C.) expressed in micrograms/ml to be determined. The results were expressed in the form of geometric averages of all the MIC's obtained, that is to say the $MIC_{50}$'s and $MIC_{90}$'s, which represent the minimum concentrations of antibiotics allowing the growth of 50 and 90% of the strains studied to be inhibited.

The following results were obtained:

| Product of example | Penicillin-resistant Staphylococci | Cefotaxime-resistant enterobacteria (35 strains) | Cefotaxime-sensitive enterobacteria (26 strains) | *Pseudomonas aeruginosa* (36 strains) |
|---|---|---|---|---|
| 1 | 0,35 | 1,17 | 0,22 | — |
| 2 | 0,21 | 1,02 | 0,14 | — |
| 3 | 0,88 | 1,68 | 0,3 | — |
| 4 | 0,42 | 0,26 | 0,098 | 0,96 |
| 5 | 0,11 | 1,06 | 0,071 | — |
| 6 | 0,25 | 2,89 | 0,33 | — |

-continued

| Product of example | Penicillin-resistant Staphylococci | Cefotaxime-resistant enterobacteria (35 strains) | Cefotaxime-sensitive enterobacteria (26 strains) | Pseudomonas aeruginosa (36 strains) |
|---|---|---|---|---|
| 7  | 0,11 | 0,96 | 0,087 | — |
| 8  | 0,57 | 0,24 | —     | 0,26 |
| 10 | 0,91 | 0,64 | —     | 0,21 |
| 11 | 0,57 | 0,26 | —     | 0,24 |
| 12 | 0,68 | 0,29 | —     | 0,29 |
| 13 | 0,78 | 0,25 | —     | 0,091 |

Various modifications of the products and method of the invention may be made without departing from the spirit or scope thereof and it is to be understood that the invention is intended to be limited only as defined in the appended claims.

What we claim is:

1. A syn isomer of a compound of the formula

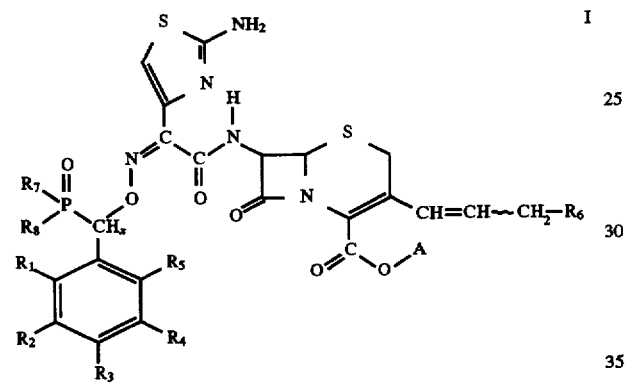

I in (R) or (S) form or an (R,S) mixture or in the form of internal salts or salts with non-toxic, pharmaceutically acceptable acids or bases wherein $R_1$, $R_2$, $R_3$ and $R_5$ are individually selected from the group consisting of hydrogen, halogen, —OH, alkyl of 1 to 4 carbon atoms optionally substituted with at least one halogen, alkoxy of 1 to 4 carbon atoms, —SH, —$NO_2$, —CN, alkylthio of 1 to 4 carbon atoms, amino, alkylamino of 1 to 4 carbon atoms, dialkylamino of 2 to 8 carbon atoms, carbamoyl, alkylaminocarbonyl of 2 to 5 carbon atoms, dialkylaminocarbonyl of 3 to 9 carbon atoms, —COOH, alkoxycarbonyl of 2 to 5 carbon atoms, acyloxy of 1 to 8 carbon atoms, and

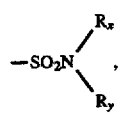

$R_x$ and $R_y$ are individually hydrogen or alkyl of 1 to 4 carbon atoms, $R_4$ is hydroxy or acyloxy of 1 to 8 carbon atoms, $R_7$ is selected from the group consisting of alkyl of 1 to 4 carbon atoms, —OH, alkoxy of 1 to 4 carbon atoms and phenyl, $R_8$ is —OH or alkoxy of 1 to 4 carbon atoms or $R_7$ and $R_8$ together are an alkylenedioxy of 2 to 8 carbon atoms, A is selected from the group consisting of hydrogen, an equivalent of an alkali metal, alkaline earth-metal, magnesium, ammonium and an amino organic base and the remainder of an easily cleavable ester or —COOA is —COO⁻, the wavy line indicates —$CH_2R_6$ is in the E or Z position, $R_6$ in its quaternary ammonium form is selected from the group consisting of

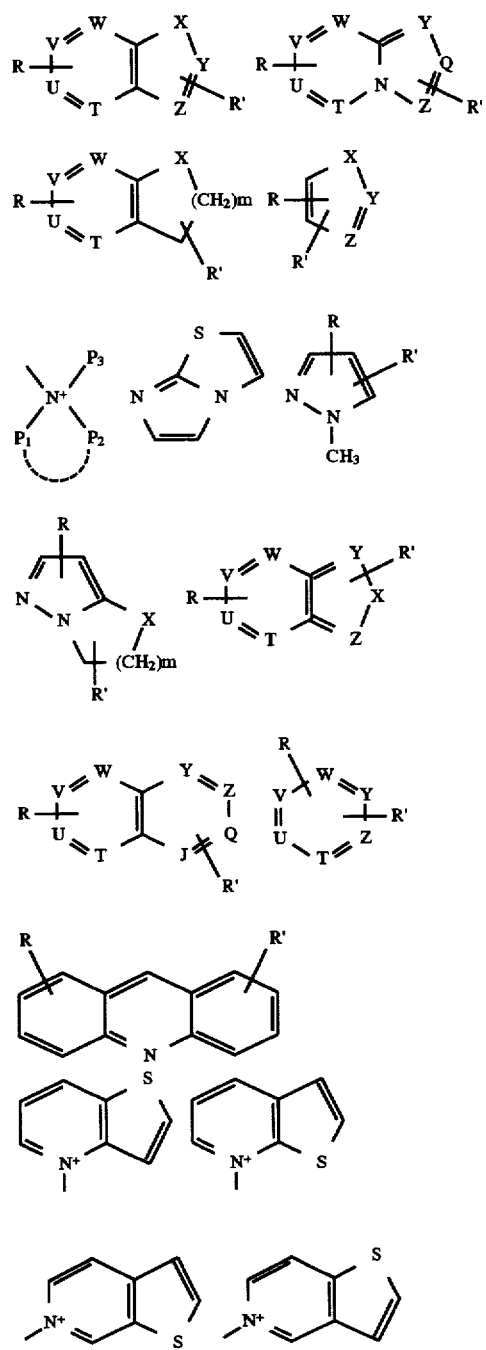

37
-continued
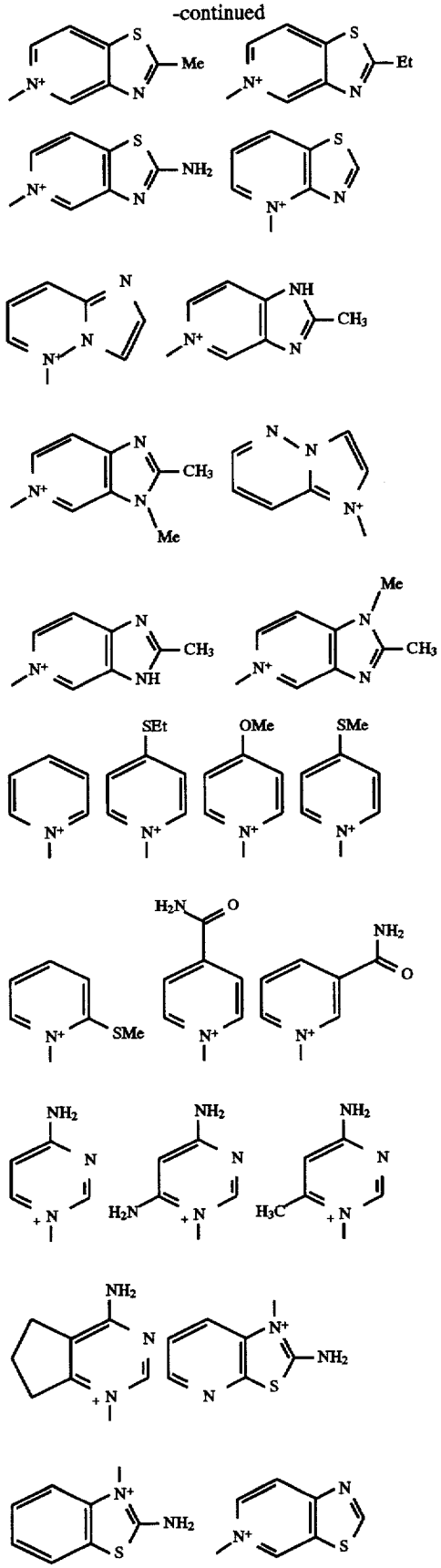
38
-continued
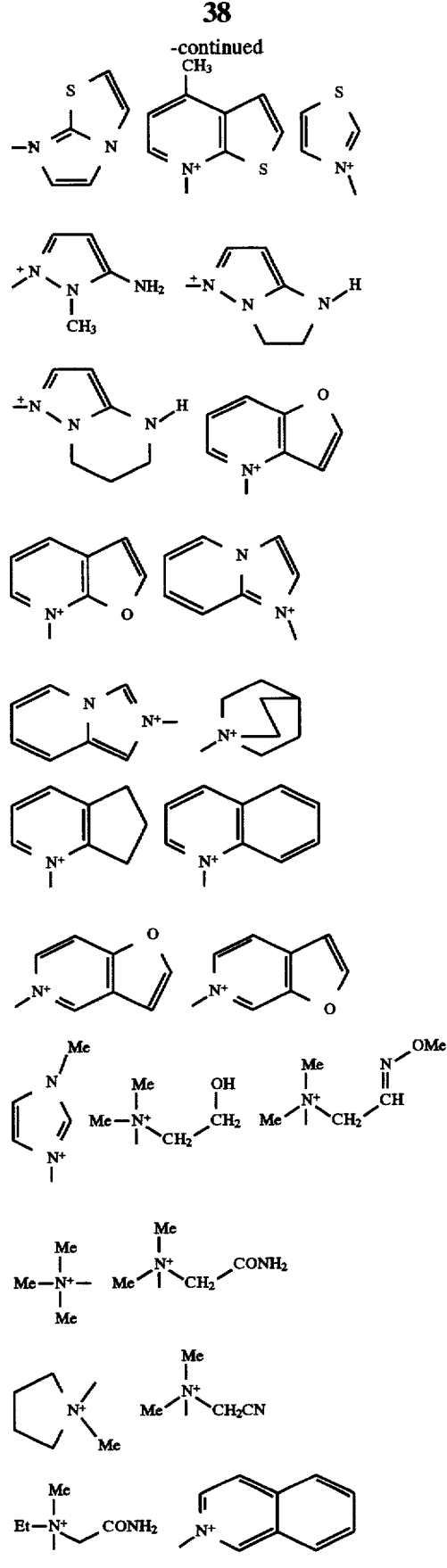

X is selected from the group consisting of —CH$_2$—, —NH—, —O— and —S—, Q, J, Y, T, U, V, W and Z are individually —CH— or —N— with each cyclic ring containing 1 to 5 heteroatoms with at least one being nitrogen and optionally substituted with at least one R or R', R and R' are individually selected from the group consisting of hydrogen, alkyl of 1 to 4 carbon atoms, alkoxy of 1 to 4 carbon atoms, halogen, —CN, —COOQ$_1$,

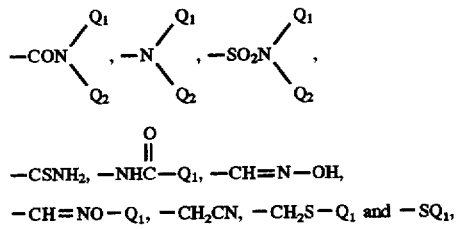

—CSNH$_2$, —NHC(=O)—Q$_1$, —CH=N—OH,

—CH=NO—Q$_1$, —CH$_2$CN, —CH$_2$S—Q$_1$ and —SQ$_1$,

Q$_1$ and Q$_2$ are individually hydrogen or alkyl of 1 to 4 carbon atoms K$_1$, K$_2$ and K$_3$ are individually alkyl of 1 to 4 carbon atoms optionally substituted by R or R' and one may be —OH or P$_1$ and P$_2$ together with the nitrogen atom to which they are attached form a 5- or 6- member heterocyclic and m is 1, 2 or 3.

2. A compound of claim 1 wherein R$_6$ is selected from the group consisting of quinolinium, isoquinolinium, 4-(methylthio)pyridinium, thieno[2,3-b]pyridinium, 1-methyl-pyrrolidinium N-methyl-N-ethyl-N-(2-amino-2-oxo-ethyl)-aminium.

3. A compound of claim 1 wherein R$_3$ and R$_4$ are —OH.
4. A compound of claim 1 wherein R$_2$ and R$_5$ are chlorine.
5. A compound of claim 1 wherein R$_2$ and R$_5$ are fluorine.
6. A compound of claim 1 wherein R$_1$ and R$_2$ are fluorine.
7. A compound of claim 1 wherein R$_2$ is methoxy and R$_1$ or R$_5$ is chlorine.

8. A compound of claim 1 selected from the group consisting of the internal salt of (6R-(3-(E)6α,7β-(Z)))1-(3-(7-(((2-amino 4-thiazolyl)-(ethoxymethylphosphinyl-(3,4-dihydroxyphenyl)-methoxy)-imino)-acetamido)-2-carboxy-8-oxo-5-thia-1-azabicyclo[4,2,0]oct-2-en-3-yl)-2-propenyl)-quinolinium, the internal salt of (6R-(3-(E)6α,7β-(Z)))7-(3-(7-(((2-amino 4-thiazolyl)-(ethoxymethylphosphinyl-(3,4-dihydroxyphenyl)-methoxy)-imino)-acetamido)-2-carboxy 8-oxo-5-thia-1-azabicyclo[4,2,0]oct-2-en-3-yl)-2-propenyl)-thieno(2,3-b)pyridinium, the internal salt of (6R-(3-(E)6α,7β-(Z)))7-(3-(7-(((2-amino-4-thiazolyl)-(hydroxymethylphosphinyl-(3,4-dihydroxyphenyl)-methoxy)-imino)-acetamido)-2-carboxy-8-oxo-5-thia-1-azabicyclo[4,2,0]oct-2-en-3-yl)-2-propenyl)thieno(2,3-b)pyridinium, the internal salt of (6R-(3-(E)6α,7β-(Z)))7-(3-(7-(((2-amino 4-thiazolyl)((2,5-dichloro-3,4-dihydroxyphenyl)-(diethoxyphosphinyl)-methoxy)-imino)-acetamido)-2-carboxy-8-oxo-5-thia-1-azabicyclo[4,2,0]oct-2-en-3-yl)-2-propenyl)-thieno(2,3-b)pyridinium, the internal salt of (6R-(3-(E)6α,7β-(Z)))7-(3-(7-(((2-amino-4-thiazolyl)-((2,5-dichloro-3,4-dihydroxyphenyl)-phosphonomethoxy)-imino)-acetamido)-2-carboxy-8-oxo 5-thia-1-azabicyclo[4,2,0]oct-2-en-3-yl)-2-propenyl)-thieno(2,3-b)pyridinium, the internal salt of (6R-(3(E)),6α,7β(Z)))7-(3-(7-(((2-amino-4-thiazolyl)-(diethoxyphosphinyl-(3,4-dihydroxy-phenyl)-methoxy)-imino)-acetamido)-2-carboxy-8-oxo-5-thia-1-azabicyclo[4,2,0]oct-2-en-3-yl)-2-propenyl)-thieno(2,3-b)-pyridinium, the internal salt of (6R-(3(E)),6α,7β(Z)))7-(3-(7-(((2-amino-4-thiazolyl)-(3,4-dihydroxyphenyl)-phosphono-methoxy)-imino)-acetamido)-2-carboxy-8-oxo-5-thia-1-azabicyclo[4,2,0]oct-2-en-3-yl)-2-propenyl)thieno (2,3-b)-pyridinium, the internal salt of (6R-(3(E),6α,7β(Z)))7-(3-(7-(((2-amino-4-thiazolyl)-((ethoxymethylphosphinyl)-(2,5-dichloro-3,4-dihydroxyphenyl)-methoxy)-imino)-acetamido)-2-carboxy-8-oxo-5-thia-1-azabicyclo[4,2, 0]oct-2-en-3-yl)-2-propenyl)-thieno(2,3-b)pyridinium (isomer A) and (isomer B), the internal salt of (6R-(3(E),6α,7β(Z)))7-(3-(7-(((2-amino-4-thiazolyl)-((hydroxymethylphosphinyl)-(2,5-dichloro-3,4-dihydroxyphenyl)-methoxy)-imino)-acetamido)-2-carboxy-8-oxo-5-thia-1-azabicyclo[4,2, 0]oct-2-en-3-yl)-2-propenyl)-thieno(2,3-b)pyridinium, the internal salt of (6R-(3(E),6α,7β(Z)))1-(3-(7-(((2-amino-4-thiazolyl)-((ethoxymethylphosphinyl)-(2,5-dichloro-3,4-dihydroxyphenyl)-methoxy)-imino)-acetamido)-2-carboxy-8-oxo-5-thia-1-azabicyclo[4,2, 0]oct-2-en-3-yl)-2-propenyl)-quinolinium (isomer A) and (isomer B), and the internal salt of (6R-(3(E),6α,7β(Z)))1-(3-(7-(((2-amino-4-thiazolyl)-(((hydroxymethylphosphinyl)-(2,5-dichloro-3,4-dihydroxyphenyl)-methoxy)-imino)-acetamido)-2-carboxy-8-oxo-5-thia-1-azabicyclo[4,2, 0]oct-2-en-3yl)-2-propenyl)-quinolinium.

9. A compound having a formula selected from the group consisting of

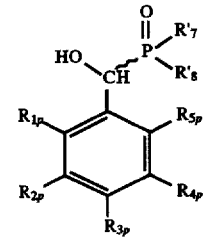

IV

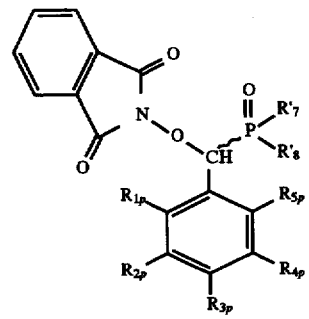

V

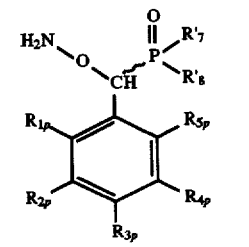

VI

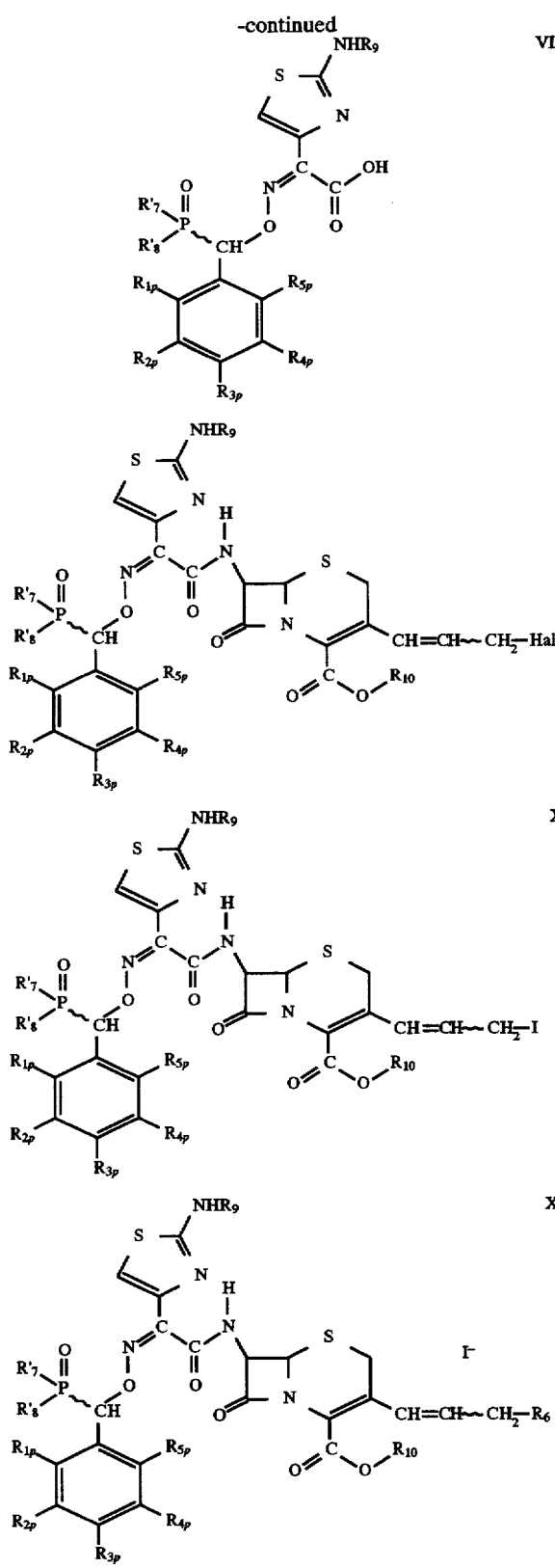

wherein $R_{1p}$, $R_{2p}$, $R_{3p}$, $R_{4p}$ and $R_{5p}$ have the definition of $R_1$, $R_2$, $R_3$, $R_4$ and $R_5$ in claim 1 with reactive functionally optionally protected, $R'_7$ is selected from the group consisting of alkyl of 1 to 4 carbon atoms, alkoxy of 1 to 4 carbon atoms and phenyl, $R'_2$ is alkoxy of 1 to 4 carbon atoms or $R'_7$ and $R'_8$ together form an alkylenedioxy of 2 to 8 carbon atoms, $R_9$ is hydrogen or an amine protective group, $R_{10}$ is the remainder of easily cleavable ester, $R_6$ has the definition of claim 1 and the wavy line has the meaning of claim 1.

10. An antibacterial composition comprising an antibactericidally effective amount of a compound of claim 1 and an inert pharmaceutical carrier.

11. A composition of claim 10 wherein the compound is selected from the group consisting of the internal salt of (6R-(3-(E)6α,7β-(Z)))1-(3-(7-(((2-amino 4-thiazolyl)-(ethoxymethylphosphinyl-(3,4-dihydroxyphenyl)-methoxy)-imino)-acetamido)-2-carboxy-8-oxo-5-thia-1-azabicyclo[4,2,0]oct-2-en-3-yl)-2-propenyl)-quinolinium, the internal salt of (6R-(3-(E)6α,7β-(Z)))7-(3-(7-(((2-amino 4-thiazolyl)-(ethoxymethylphosphinyl-(3,4-dihydroxyphenyl)-methoxy)-imino)-acetamido)-2-carboxy 8-oxo-5-thia-1-azabicyclo[4,2,0]oct-2-en-3-yl)-2-propenyl)-thieno(2,3-b)pyridinium, the internal salt of (6R-(3-(E)6α,7β-(Z)))7-(3-(7-(((2-amino-4-thiazolyl)-(hydroxymethylphosphinyl-(3,4-dihydroxyphenyl)-methoxy)-imino)-acetamido)-2-carboxy-8-oxo-5-thia-1-azabicyclo[4,2,0]oct-2-en-3-yl)-2-propenyl)thieno(2,3-b)pyridinium, the internal salt of (6R-(3-(E)6α,7β-(Z)))7-(3-(7-(((2-amino 4-thiazolyl)((2,5-dichloro-3,4-dihydroxyphenyl)-(diethoxyphosphinyl)-methoxy)-imino)-acetamido)-2-carboxy-8-oxo-5-thia-1-azabicyclo[4,2,0]oct-2-en-3-yl)-2-propenyl)-thieno(2,3-b)pyridinium, the internal salt of (6R-(3-(E)6α,7β-(Z)))7-(3-(7-(((2-amino-4-thiazolyl)-((2,5-dichloro-3,4-dihydroxyphenyl)-phosphonomethoxy)-imino)-acetamido)-2-carboxy-8-oxo 5-thia-1-azabicyclo[4,2,0]oct-2-en-3-yl)-2-propenyl)-thieno(2,3-b)pyridinium, the internal salt of (6R-(3(E),6α,7β(Z)))7-(3-(7-(((2-amino-4-thiazolyl)-(diethoxyphosphinyl-(3,4-dihydroxy-phenyl)-methoxy)-imino)-acetamido)-2-carboxy-8-oxo-5-thia-1-azabicyclo[4,2,0]oct-2-en-3-yl)-2-propenyl)-thieno(2,3-b)-pyridinium, the internal salt of (6R-(3(E),6α,7β(Z)))7-(3-(7-(((2-amino-4-thiazolyl)-(3,4-dihydroxyphenyl)-phosphonomethoxy)-imino)-acetamido)-2-carboxy-8-oxo-5-thia-1-azabicyclo[4,2,0]oct-2-en-3-yl)-2-propenyl)thieno(2,3-b)-pyridinium, the internal salt of (6R-(3(E),6α,7β(Z)))7-(3-(7-(((2-amino-4-thiazolyl)-((ethoxymethylphosphinyl)-(2,5-dichloro-3,4-dihydroxyphenyl)-methoxy)-imino)-acetamido)-2-carboxy-8-oxo-5-thia-1-azabicyclo[4,2,0]oct-2-en-3-yl)-2-propenyl)-thieno(2,3-b)pyridinium (isomer A) and (isomer B), the internal salt of (6R-(3(E),6α,7β(Z)))7-(3-(7-(((2-amino-4-thiazolyl)-((hydroxymethylphosphinyl)-(2,5-dichloro-3,4-dihydroxyphenyl)-methoxy)-imino)-acetamido)-2-carboxy-8-oxo-5-thia-1-azabicyclo[4,2,0]oct-2-en-3-yl)-2-propenyl)-thieno(2,3-b)pyridinium, the internal salt of (6R-(3(E),6α,7β(Z)))1-(3-(7-(((2-amino-4-thiazolyl)-((ethoxymethylphosphinyl)-(2,5-dichloro-3,4-dihydroxyphenyl)-methoxy)-imino)-acetamido)-2-carboxy-8-oxo-5-thia-1-azabicyclo[4,2,0]oct-2-en-3-yl)-2-propenyl)-quinolinium (isomer A) and (isomer B), and the internal salt of (6R-(3(E),6α,7β(Z)))1-(3-(7-(((2-amino-4-thiazolyl)-(((hydroxymethylphosphinyl)-(2,5-dichloro-3,4-dihydroxyphenyl)-methoxy)-imino)-acetamido)-2-carboxy-8-oxo-5-thia-1-azabicyclo[4,2,0]oct-2-en-3yl)-2-propenyl)-quinolinium.

12. A method of combatting bacterial infections in warm-blooded animals comprising administering to warm-blooded animals an antibactericidally effective amount of a compound of claim 1.
13. A method of claim 12 wherein $R_6$ is selected from the group consisting of
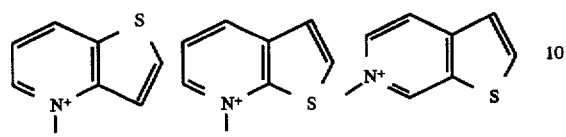
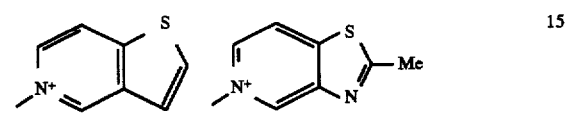
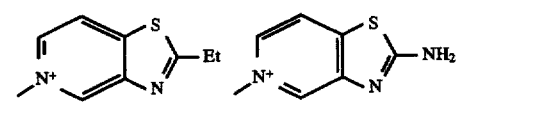
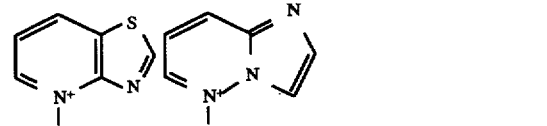
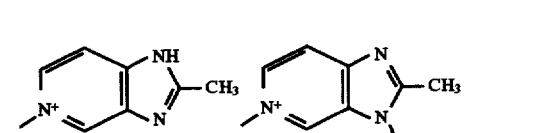
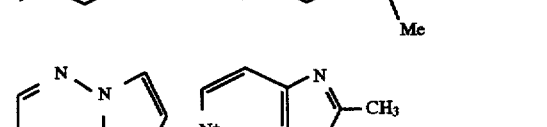
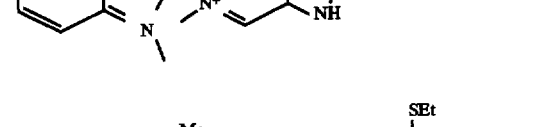
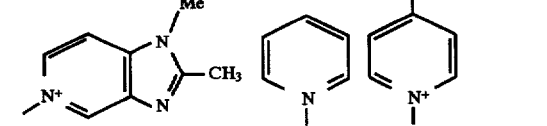
-continued
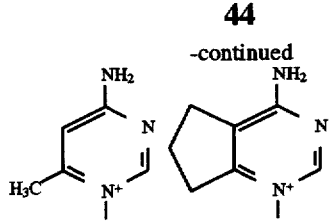
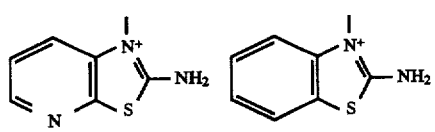
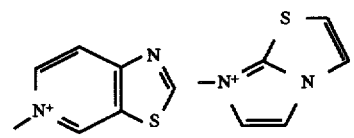
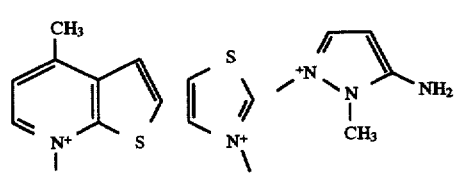
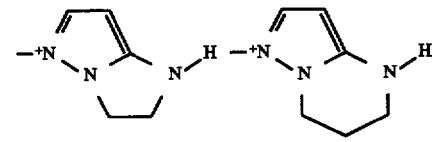
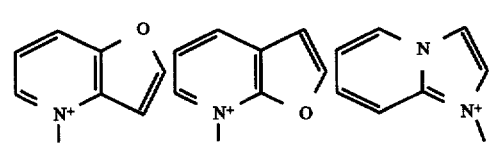
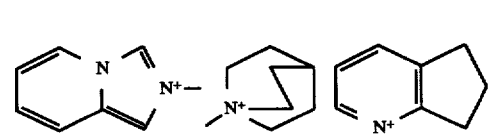
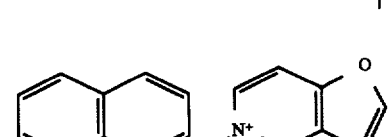
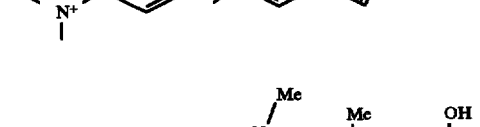
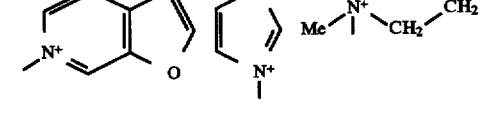
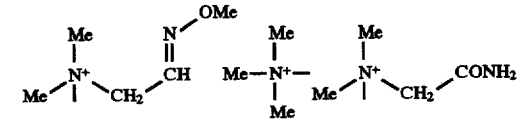

-continued

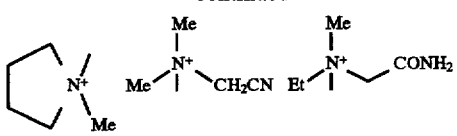

and

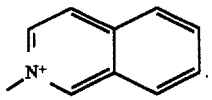

14. A method of claim 12 wherein $R_6$ is selected from the group consisting of quinolinium, isoquinolinium, 4-(methylthio)pyridinium, thieno[2,3-b]pyridinium, 1-methyl-pyrrolidinium, N-methyl-N-ethyl-N-(2-amino-2-oxo-ethyl)-aminium.

15. A method of claim 12 wherein $R_3$ and $R_4$ are —OH.

16. A method of claim 12 wherein $R_2$ and $R_5$ are chlorine.

17. A method of claim 12 wherein $R_2$ and $R_5$ are fluorine.

18. A method of claim 12 wherein $R_1$ and $R_2$ are fluorine.

19. A method of claim 12 wherein $R_2$ is methoxy and $R_1$ or $R_5$ is chlorine.

20. A compound of claim 1 wherein $R_6$ is selected from the group consisting of

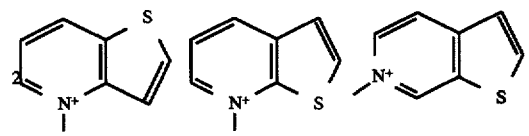
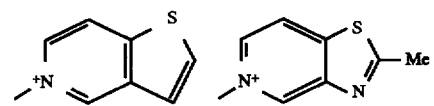
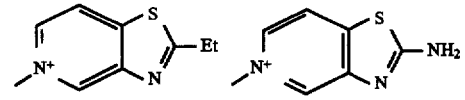
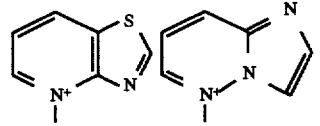
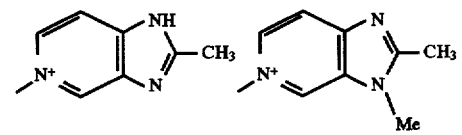
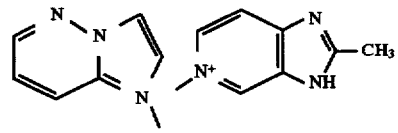

-continued

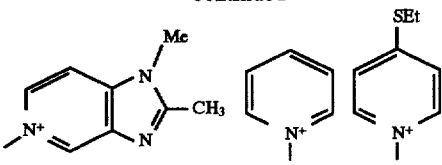
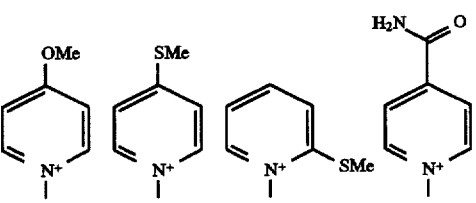
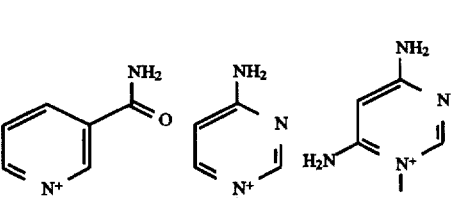
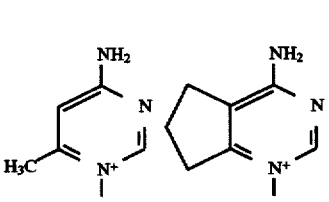
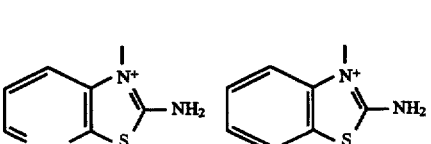
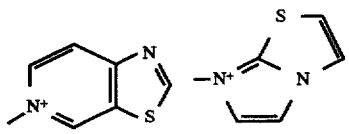
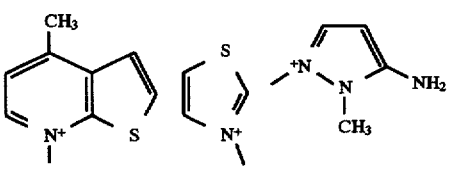
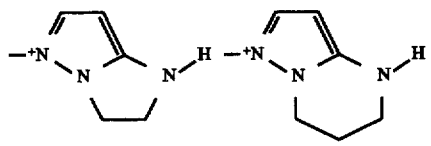
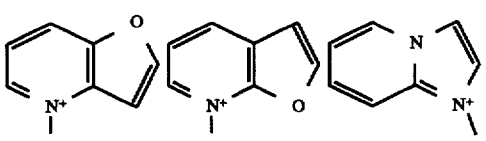

47
-continued
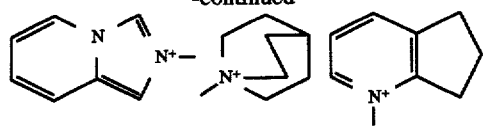
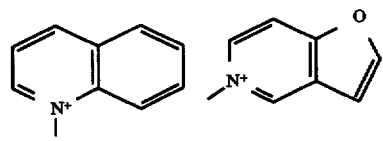
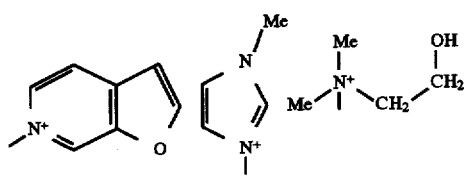
48
-continued
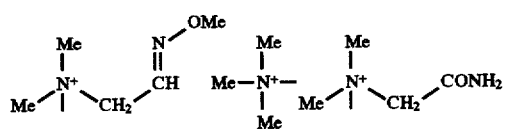
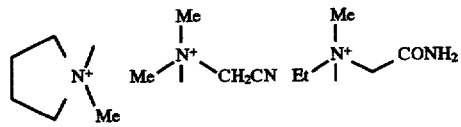
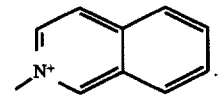
* * * * *